US012747199B2

(12) United States Patent
Xiang et al.

(10) Patent No.: US 12,747,199 B2
(45) Date of Patent: Sep. 29, 2026

(54) CRYSTALLINE 4-((L-VALYL)OXY)BUTANOIC ACID

(71) Applicant: XWPHARMA LTD., Grand Cayman (KY)

(72) Inventors: Jia-Ning Xiang, Fremont, CA (US); Xuesong Xu, Fremont, CA (US); Xuan Zhang, Fremont, CA (US); James Tien, Taoyuan (TW); Hao-Wei Shih, New Taipei City (TW); Hsin-Yi Huang, New Taipei City (TW)

(73) Assignee: XWPharma Ltd., Grand Cayman (KY)

( * ) Notice: Subject to any disclaimer, the term of this patent is extended or adjusted under 35 U.S.C. 154(b) by 335 days.

(21) Appl. No.: 18/239,265

(22) Filed: Aug. 29, 2023

(65) Prior Publication Data

US 2024/0092727 A1 Mar. 21, 2024

Related U.S. Application Data

(60) Provisional application No. 63/417,205, filed on Oct. 18, 2022, provisional application No. 63/404,070, filed on Sep. 6, 2022.

(51) Int. Cl.
*C07C 229/24* (2006.01)
*A61K 9/16* (2006.01)
*A61K 31/221* (2006.01)

(52) U.S. Cl.
CPC .............. *C07C 229/24* (2013.01); *A61K 9/16* (2013.01); *A61K 31/221* (2013.01); *C07B 2200/13* (2013.01)

(58) Field of Classification Search
CPC .................................................... C07C 229/24
USPC .......................................................... 514/551
See application file for complete search history.

(56) References Cited

U.S. PATENT DOCUMENTS

| | | | |
|---|---|---|---|
| 10,640,451 | B2 | 5/2020 | Xiang et al. |
| 10,774,031 | B2 | 9/2020 | Xiang et al. |
| 11,279,669 | B2 | 3/2022 | Xiang et al. |
| 11,395,801 | B2 | 7/2022 | Xiang et al. |
| 2002/0128301 | A1 | 9/2002 | Zhou et al. |
| 2021/0393537 | A1 | 12/2021 | Karaborni et al. |

FOREIGN PATENT DOCUMENTS

| | | | | |
|---|---|---|---|---|
| WO | 1999/041275 A1 | 8/1999 | |
| WO | 1999/051613 A1 | 10/1999 | |
| WO | 2010/124046 A1 | 10/2010 | |
| WO | 2012/112492 A1 | 8/2012 | |
| WO | 2014/031840 A1 | 2/2014 | |
| WO | 2017/049470 A1 | 3/2017 | |
| WO | 2017/050259 A1 | 3/2017 | |
| WO | WO-2022020621 A1 * | 1/2022 | ........... A61K 9/0095 |

OTHER PUBLICATIONS

International Search Report and Written Opinion for PCT Application No. PCT/US2023/031743, mailed on Dec. 14, 2023, 12 pages.
Search Report and Written Opinion for PCT Application No. PCT/US2020/066047, mailed on Mar. 23, 2021.
International Preliminary Report on Patentability for PCT Application No. PCT/US2020/066047, mailed on May 17, 2022.
Non-Final Office Action for U.S. Appl. No. 17/673,335, mailed on Feb. 14, 2023.
Notice of Allowance for U.S. Appl. No. 17/673,335, mailed on Apr. 27, 2023.
Notice of Allowance for U.S. Appl. No. 17/351,550, mailed on Feb. 17, 2022.

* cited by examiner

*Primary Examiner* — Jeffrey H Murray
*Assistant Examiner* — Rilla Marie Samsell
(74) *Attorney, Agent, or Firm* — Sheppard Mullin Richter & Hampton LLP

(57) ABSTRACT

Crystalline 4-((L-valyl)oxy)butanoic acid, methods of preparing crystalline 4-((L-valyl)oxy)butanoic acid, pharmaceutical compositions of crystalline 4-((L-valyl)oxy)butanoic acid, and methods of treatment using crystalline 4-((L-valyl)oxy)butanoic acid are disclosed.

30 Claims, 2 Drawing Sheets

CRYSTALLINE 4-((L-VALYL)OXY)BUTANOIC ACID

This application claims the benefit under 35 U.S.C. § 119(e) of U.S. Provisional Application No. 63/417,205 filed on Oct. 18, 2022, and U.S. Provisional Application No. 63/404,070 filed on Sep. 6, 2022, each of which is incorporated by reference in its entirety.

FIELD

The invention relates to crystalline 4-((L-valyl)oxy)butanoic acid, methods of preparing the crystalline 4-((L-valyl)oxy)butanoic acid, pharmaceutical compositions containing the crystalline 4-((L-valyl)oxy)butanoic acid, and methods of treatment using the crystalline 4-((L-valyl)oxy)butanoic acid.

BACKGROUND 4-((L-Valyl)oxy)butanoic acid is a prodrug of γ-hydroxybutyric acid (GHB). GHB is useful for treating sleep disorders such as excessive daytime sleepiness associated with narcolepsy and cataplexy associated with narcolepsy.

SUMMARY

According to the present invention a compound is crystalline 4-((L-valyl)oxy)butanoic acid:

(1)

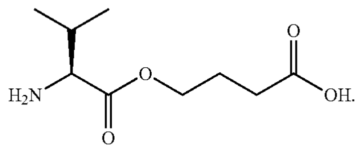

According to the present invention, pharmaceutical compositions comprise a compound according to the present invention.

According to the present invention, oral dosage forms comprise a compound according to the present invention or a pharmaceutical composition according to the present invention.

According to the present invention, kits comprise a compound according to the present invention, a pharmaceutical composition according to the present invention, or an oral dosage form according to the present invention.

According to the present invention, methods of treating a disease in a patient comprise administering to a patient in need of such treatment a therapeutically effective amount of a compound according to the present invention, a pharmaceutical composition according to the present invention, or an oral dosage form according to the present invention, wherein the disease can be treated with γ-hydroxybutyric acid.

BRIEF DESCRIPTION OF THE DRAWINGS

The drawings described herein are for illustration purposes only. The drawings are not intended to limit the scope of the present disclosure.

DETAILED DESCRIPTION

Figure 1:
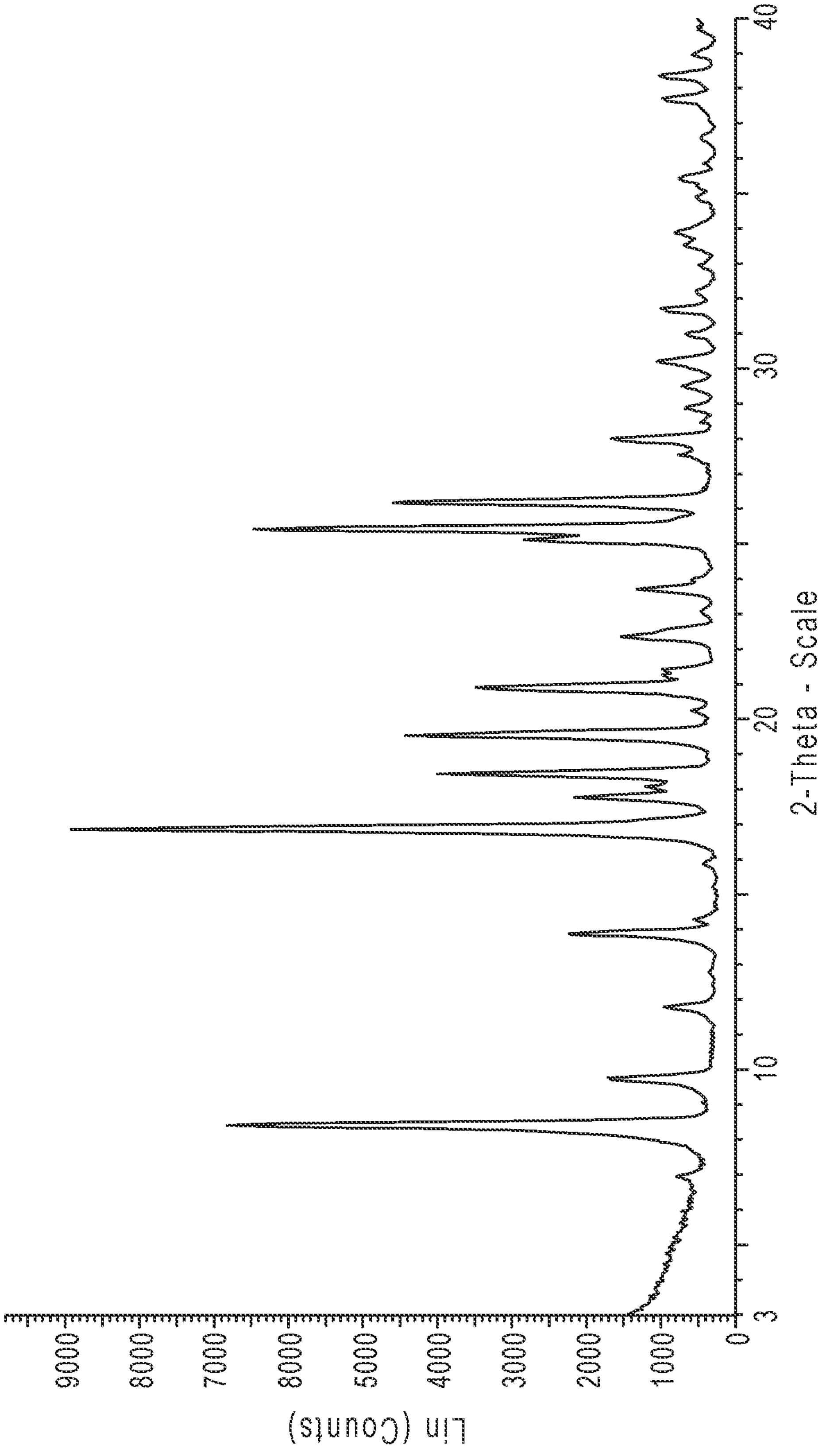
FIG. 1 shows an X-ray powder diffraction (XRPD) pattern of crystalline 4-((L-valyl)oxy)butanoic acid.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Immediate release" refers to a pharmaceutical composition that releases substantially all of a pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Modified release" pharmaceutical compositions include controlled release formulations, delayed release formulations, extended-release formulations, sustained release formulations, timed release formulations, pulsatile release formulations, and pH-dependent release formulations. These formulations are intended to release a pharmaceutically active ingredient from the pharmaceutical composition at a desired rate and/or at a desired time following oral administration by a patient and/or at a certain location or locations within the gastrointestinal tract and/or at a certain pH within the gastrointestinal tract. The USP defines a modified release system as one in which the time course or location of drug release or both, are chosen to accomplish objectives of therapeutic effectiveness or convenience not fulfilled by immediate release dosage forms. A modified release oral dosage form can include extended release and delayed-release components. A delayed release dosage form is one that releases a drug all at once at a time other than promptly after administration. A modified release formulation can include delayed-release using enteric coatings, site-specific or timed release such as for colonic delivery, extended-release formulations including, for example, formulations capable of providing zero-order, first-order, or biphasic release profiles, and programmed release such as pulsatile and delayed extended release.

"Sustained release" pharmaceutical compositions and coatings provide for a dissolution rate over an extended period of time following oral administration. Granulations comprising granules having a sustained release coating can be referred to as sustained release granulations. A pharmaceutical composition comprising a sustained release granulation can be referred to as a sustained release pharmaceutical composition.

"pH-release" pharmaceutical compositions and coatings provide for an increased dissolution rate at an intended pH.

"Pulsatile release" pharmaceutical compositions and coatings exhibit an increased dissolution rate at intervals, where the release intervals can be determined by time, exposure to internal stimuli, or exposure to external stimuli. Examples of pulsatile-release systems include capsular systems, osmotic systems, systems having erodible membranes, and systems having a rupturable coating. Examples of stimuli include temperature, chemicals, electrical stimuli, and magnetic stimuli.

"Timed-release" pharmaceutical compositions and coatings have a dissolution rate that is a function of time. A time-release pharmaceutical composition or coating includes, for example, delayed release, sustained release, and extended-release pharmaceutical compositions and coatings.

"Delayed release" pharmaceutical compositions and coatings provide for an increased dissolution rate at an intended time after administration.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to 4-((L-valyl)oxy) butanoic acid and at least one pharmaceutically acceptable vehicle, with which 4-((L-valyl)oxy)butanoic acid is administered to a patient. Pharmaceutically acceptable vehicles are known in the art.

"Disease" refers to a disease, disorder, condition, or symptom of any of the foregoing.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety typically via a functional group, to a drug. For example, referring to 4-((L-valyl)oxy)butanoic acid, a $NH_2$—CH(—$CH_3$)$_2$)— promoiety is bonded to γ-hydroxybutyric acid. 4-((L-Valyl)oxy)butanoic acid is a prodrug of γ-hydroxybutyric acid that can be metabolized within a patient's body to release γ-hydroxybutyric acid.

"Promoiety" refers to a group bonded to a drug, typically to a functional group of the drug, via a bond or bonds that are cleavable under specified conditions of use. The bond or bonds between the drug and promoiety may be cleaved by enzymatic or non-enzymatic processes. Under the conditions of use, for example following administration to a patient, the bond or bonds between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature or pH. The agent may be endogenous to the conditions of use, such as an enzyme present in the systemic circulation of a patient to which the prodrug is administered or the acidic conditions of the stomach or the agent may be supplied exogenously. Compounds provided by the present disclosure are prodrugs of γ-hydroxybutyric aced. The promoiety of 4-((L-valyl) oxy)butanoic acid has the structure:

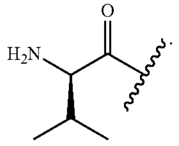 [SMILES: *C(=O)[C@H](N)C(C)C]

The promoiety is cleaved in vivo to γ-hydroxybutyric acid in the systemic circulation of a patient.

"Curing" a disease refers to eliminating a disease or disorder or eliminating a symptom of a disease or disorder.

"Sealed storage stability" refers to the stability of a compound that is enclosed within two sealed polyethylene bags with a desiccant material placed between the two polyethylene bags and the two sealed polyethylene bags are enclosed within a sealed one-layer aluminum bag.

"Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, reducing the severity of one or more clinical symptom of the disease or disorder, delaying the onset of one or more clinical symptoms of the disease or disorder, mitigating one or more clinical symptoms of the disease or disorder and/or stabilizing the disease or disorder or one or more clinical symptoms of the disease or disorder. "Treating" or "treatment" of a disease or disorder includes producing a clinically beneficial effect without curing the underlying disease or disorder.

"Therapeutically effective amount" refers to the amount of a compound such as pharmaceutically active ingredient that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Bulk density can be determined according to USP 616, Method 1.

Tapped bulk density can be determined according to USP 616.

Specific surface area can be determined by laser diffraction.

The Hausner Ratio can be determined according to USP 1174.

The parameter D90 refers to the point in the size distribution of a sample, up to and including which 90% of the total volume of material in the sample is contained. For example, for a D90 of 400 μm, 90% of the sample volume has a size of 400 μm or less D50 is the size below which 50% of the total volume of material in the sample is contained. Similarly, D10 refers to the size below which 10% of the total volume of material in the sample is contained. The volume distribution of the sample can be determined by laser diffraction or by sieve analysis.

Equivalents of γ-hydroxybutyric acid such as gm-equivalents of γ-hydroxybutyric acid refers to the grams of γ-hydroxybutyric acid in an amount of crystalline 4-((L-valyl)oxy)butanoic acid. The amount of gm-equivalents of γ-hydroxybutyric acid can be determined by multiplying the amount in grams of crystalline 4-((L-valyl)oxy)butanoic acid by 0.512. For example, 10 grams of 4-((L-valyl)oxy)butanoic acid corresponds to 5.12 gm-equivalents of γ-hydroxybutyric acid.

Reference is now made to crystalline 4-((L-valyl)oxy)butanoic acid, methods of making crystalline 4-((L-valyl)oxy)butanoic acid, pharmaceutical compositions comprising crystalline 4-((L-valyl)oxy)butanoic acid, and uses of crystalline 4-((L-valyl)oxy)butanoic acid. The disclosed crystalline 4-((L-valyl)oxy)butanoic acid, pharmaceutical compositions, methods, and uses are not intended to be limiting of the claims. To the contrary, the claims are intended to cover all alternatives, modifications, and equivalents.

Crystalline 4-((L-valyl)oxy)butanoic acid, is a stable crystalline form of 4-((L-valyl)oxy)butanoic acid. Crystalline 4-((L-valyl)oxy)butanoic acid has the structure:

(1)

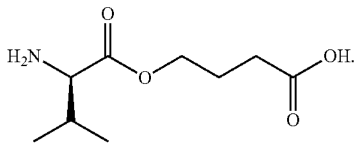

4-((L-Valyl)oxy)butanoic acid is also referred to as (5)-4-(2-amino-3-methylbutanoyloxy)butanoic acid.

Methods of synthesizing 4-((L-valyl)oxy)butanoic acid and properties of 4-((L-valyl)oxy)butanoic acid are disclosed in U.S. Pat. Nos. 10,457,627 and 11,279,669, each of which is incorporated by reference in its entirety.

Crystalline 4-((L-valyl)oxy)butanoic acid can be prepared as described in Example 1.

4-((L-valyl)oxy)butanoic acid can be characterized by an X-ray powder diffraction (XRPD) pattern comprising characteristic diffraction peaks at least at 8.28°±0.20°, 16.75°±0.20°, and 25.33±0.20° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.2°, 16.75°±0.20°, 17.64°±0.20°, 18.31°±0.20°, 19.42°±0.20°, 20.79°±0.20°, 25.33±0.20°, and 26.08°±0.20° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.20°, 9.58°±0.20°, 13.75°±0.20°, 16.75°±0.20°, 17.64°±0.20°, 18.31°±0.20°, 19.42°±0.20°, 20.79°±0.20°, 24.98°±0.20°, 25.33±0.20°, and 26.08°±0.20° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.20°, 9.58°±0.20°, 11.63°±0.20°, 13.75°±0.02°, 16.75°±0.20°, 17.64°±0.20°, 19.93°±0.20°, 18.31°±0.20°, 19.42°±0.20°, 20.79°±0.20°, 22.22°±0.20°, 23.58°±0.20°, 24.98°±0.20°, 25.33±0.20°, and 26.08°±0.20° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.10°, 16.75°±0.10°, and 25.33±0.10° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.10°, 16.75°±0.10°, 17.64°±0.10°, 18.31°±0.10°, 19.42°±0.10°, 20.79°±0.10°, 25.33±0.10°, and 26.08°±0.10° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.10°, 9.58°±0.10°, 13.75°±0.10°, 16.75°±0.10°, 17.64°±0.10°, 18.31°±0.10°, 19.42°±0.10°, 20.79°±0.10°, 24.98°±0.10°, 25.33±0.10°, and 26.08°±0.10° expressed as 2θ angles determined using Cu-Kα radiation.

Crystalline 4-((L-valyl)oxy)butanoic acid can be characterized by an XRPD pattern comprising characteristic diffraction peaks at least at 8.28°±0.10°, 9.58°±0.10°, 11.63°±0.10°, 13.75°±0.10°, 16.75°±0.10°, 17.64°±0.10°, 19.93°±0.10°, 18.31°±0.10°, 19.42°±0.10°, 20.79°±0.10°, 22.22°±0.10°, 23.58°±0.10°, 24.98°±0.10°, 25.33±0.10°, and 26.08°±0.10° expressed as 2θ angles determined using Cu-Kα radiation.

Crystalline 4-((L-valyl)oxy)butanoic acid can be characterized by an XRPD pattern as shown in FIG. 1.

Crystalline 4-((L-valyl)oxy)butanoic acid can have a melting onset temperature, for example, from 135° C. to 141° C., such as from 136° C. to 140° C., or from 137° C. to 139° C., where the melting onset temperature is determined by differential scanning calorimetry.

Crystalline 4-((L-valyl)oxy)butanoic acid can have a melting onset temperature, for example, of 137.7° C.±1.0° C., such as 137.7° C.±0.5° C., 137.7° C.±0.2° C., or 137.7° C.±0.1° C., where the melting onset temperature is determined by differential scanning calorimetry.

Crystalline 4-((L-valyl)oxy)butanoic acid can have a melting enthalpy, for example, from 197 J/g to 207 J/g, from 199 J/g to 205 J/g, from 200 J/g to 204 J/g, or from 201 J/g to 203 J/g, where the melting enthalpy is determined by differential scanning calorimetry.

Crystalline 4-((L-valyl)oxy)butanoic acid can have a melting enthalpy, for example, of 202.2 J/g+1.0 J/g, such as 202.2 J/g+0.5 J/g, 202.2 J/g+0.2 J/g, or 202.2 J/g+0.1 J/g, where the melting enthalpy is determined by differential scanning calorimetry.

Crystalline 4-((L-valyl)oxy)butanoic acid can have a melting peak temperature, for example, from 138.0° C. to 142.0° C., from 138.5° C. to 141.5° C., from 139.0° C. to 141.0° C., or from 139.5° C. to 140.5° C., where the melting peak temperature is determined by differential scanning calorimetry.

Crystalline 4-((L-valyl)oxy)butanoic acid can have a melting peak temperature, for example, at 139.9° C.±2.0° C., such as 139.9° C.±1.0° C., or 139.9° C.±0.5° C., where the melting peak temperature is determined by differential scanning calorimetry.

Figure 2:
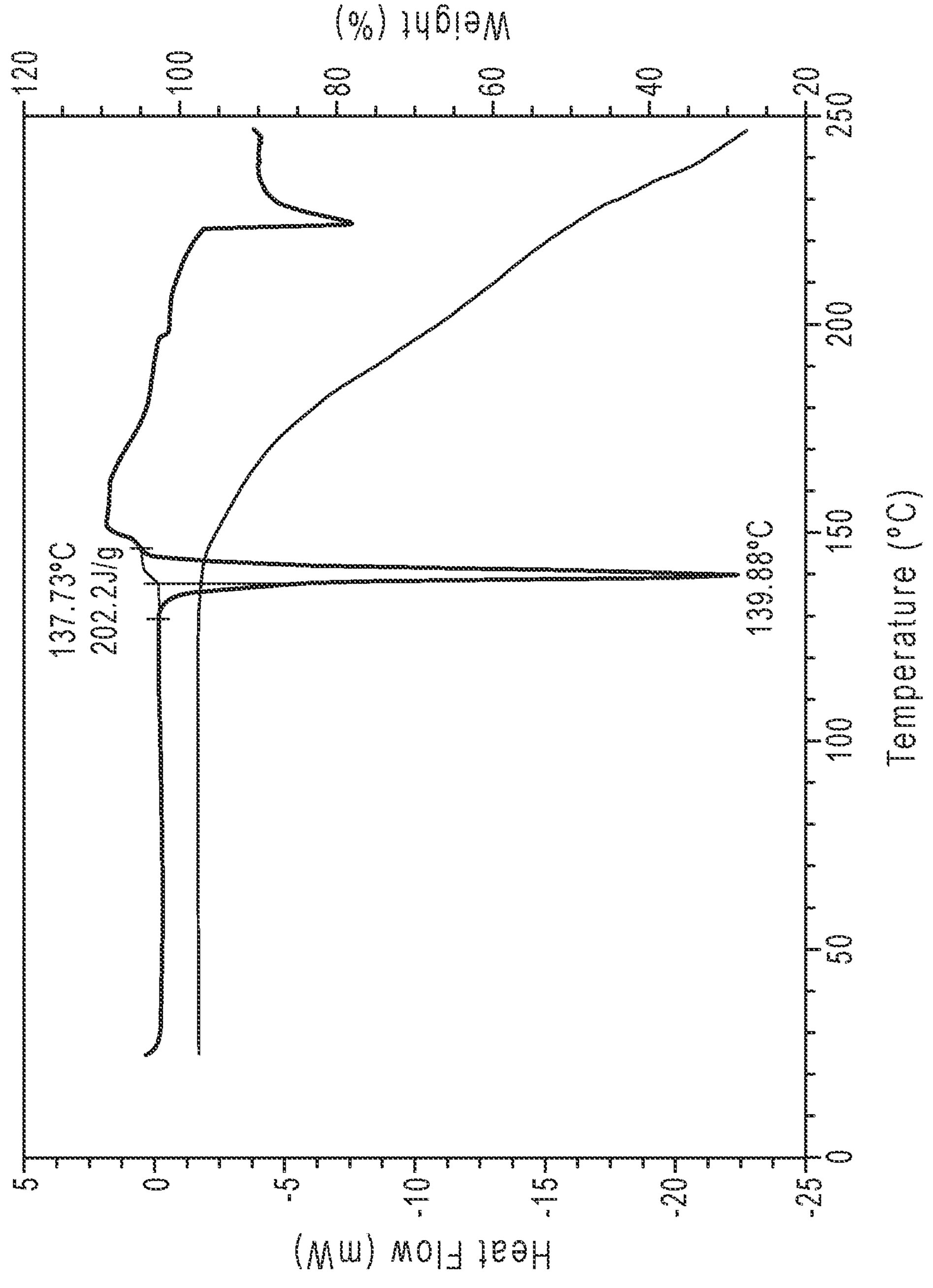
FIG. 2 shows a differential scanning calorimetry (DSC) and thermogravimetric analysis (TGA) thermograms of crystalline 4-((L-valyl)oxy)butanoic acid.

Crystalline 4-((L-valyl)oxy)butanoic acid can exhibit a differential scanning calorimetry curve as shown in FIG. 2.

Crystalline 4-((L-valyl)oxy)butanoic acid can have a weight loss, for example, from 0.16% to 0.36% at a temperature from 20° C. to 70° C., such as from 0.18% to 0.34% at a temperature from 20° C. to 70° C., from 0.20% to 0.32% at a temperature from 20° C. to 70° C., or from 0.22% to 0.30% at a temperature from 20° C. to 70° C., where the weight loss is determined by thermogravimetric analysis at a scan rate of 2° C./min.

Crystalline 4-((L-valyl)oxy)butanoic acid can have a weight loss, for example, of 0.26%±0.20%, such as 0.26%±0.10%, or 0.26%±0.05% at a temperature from 20° C. to 70° C., where the weight loss is determined by thermogravimetric analysis at a scan rate of 2° C./min.

Crystalline 4-((L-valyl)oxy)butanoic acid provided by the present disclosure can exhibit a differential thermal calorimetry curve as substantially shown in FIG. 2.

Crystalline 4-((L-valyl)oxy)butanoic acid can have a water content, for example, from 5.8 mol % to 6.6 mol %, such as from 5.9 mol % to 6.5 mol %, from 6.0 mol % to 6.4 mol %, from 6.1 mol % to 6.3 wt %, or 6.2 mol %, where mol % is based on the total moles of 4-((L-valyl)oxy) butanoic acid and water in the crystalline 4-((L-valyl)oxy) butanoic acid.

Crystalline 4-((L-valyl)oxy)butanoic acid can have a water content, for example, of less than 5 wt %, less than 4 wt %, less than 3 wt %, less than 2 wt %, less than 1 wt %, less than 0.8 wt %, less than 0.6 wt %, less than 0.4 wt %, less than 0.2 wt %, or less than 0.1 wt %, where wt % is based on the total weight of 4-((L-valyl)oxy)butanoic acid and water in the crystalline 4-((L-valyl)oxy)butanoic acid.

The water content of crystalline 4-((L-valyl)oxy)butanoic acid can be determined using Karl Fischer analysis.

Crystalline 4-((L-valyl)oxy)butanoic acid is substantially stable under sealed storage conditions.

For example, following one month, 3 months and/or six months of sealed storage at 25° C./60% RH crystalline 4-((L-valyl)oxy)butanoic acid can have a water content, for example of less than 5 wt %, less than 4 wt %, less than 3 wt %, less than 2 wt %, less than 1 wt %, less than 0.8 wt %, less than 0.6 wt %, less than 0.4 wt %, less than 0.2 wt %, or less than 0.1 wt %, where wt % is based on the total weight of 4-((L-valyl)oxy)butanoic acid and water in the crystalline 4-((L-valyl)oxy)butanoic acid, the water content is determined using Karl Fischer analysis.

For example, after 36 months of sealed storage at 25° C./65% RH the water content can be less than 2.5 wt % or less than 2.0 wt %, where wt % is based on the total weight of the sample of crystalline 4-((L-valyl)oxy)butanoic acid. Crystalline 4-((L-valyl)oxy)butanoic acid was not observed to form hydrates.

Crystalline 4-((L-valyl)oxy)butanoic acid can have a purity, for example, of greater than 95 wt %, greater than 96 wt %, greater than 97 wt %, greater than 98 wt %, greater than 99 wt %, greater than 99.2 wt %, greater than 99.4 wt %, greater than 99.6 wt %, or greater than 99.8 wt %, where wt % is based on the total weight of the sample of crystalline 4-((L-valyl)oxy)butanoic acid, and purity is determined using high pressure liquid chromatography.

Crystalline 4-((L-valyl)oxy)butanoic acid can have an impurity content, for example, of less than 5 wt %, less than 4 wt %, less than 3 wt %, less than 2 wt %, less than 1 wt %, less than 0.8 wt %, less than 0.6 wt %, less than 0.4 wt %, less than 0.2 wt %, or less than 0.1 wt %, where wt % is based on the total weight of the sample of crystalline 4-((L-valyl)oxy)butanoic acid, and purity is determined using high pressure liquid chromatography.

Following 1 month, 3 months and/or 6 months of storage at 25° C./65% RH crystalline 4-((L-valyl)oxy)butanoic acid can have an impurity content, for example, of less than 5 wt %, less than 4 wt %, less than 3 wt %, less than 2 wt %, less than 1 wt %, less than 0.8 wt %, less than 0.6 wt %, less than 0.4 wt %, less than 0.2 wt %, or less than 0.1 wt %, where wt % is based on the total weight of the sample of crystalline 4-((L-valyl)oxy)butanoic acid, and purity is determined using high pressure liquid chromatography.

The impurity content of crystalline 4-((L-valyl)oxy)butanoic acid can be determined using high pressure liquid chromatography.

Crystalline 4-((L-valyl)oxy)butanoic acid can have a chiral purity, for example, of greater than 98%, greater than 99%, greater than 99.2%, greater than 99.4%, greater than 99.6%, or greater than 99.8%, where percent (%) is based on the total moles of crystalline 4-((L-valyl)oxy)butanoic acid, and chiral purity is determined using high pressure liquid chromatography.

Un-milled crystalline 4-((L-valyl)oxy)butanoic acid can have a particle size distribution characterized by a D10 of 11.8 μm, a D50 of 34.0 μm, and a D90 of 72.3 μm, where particle size is determined by sieve analysis or by laser diffraction.

Un-milled crystalline 4-((L-valyl)oxy)butanoic acid can have a particle size distribution characterized by a D10 from 9 μm to 15 μm, a D50 of 31 μm to 37 μm, and a D90 of 69 μm to 73 μm, where particle size is determined by sieve analysis or by laser diffraction.

Un-milled crystalline 4-((L-valyl)oxy)butanoic acid can have a particle size distribution characterized by a D10 from 7 μm to 17 μm, a D50 of 29 μm to 39 μm, and a D90 of 67 μm to 75 μm, where particle size is determined by sieve analysis or by laser diffraction.

Un-milled crystalline 4-((L-valyl)oxy)butanoic acid can have a particle size distribution characterized by a D[4,3] from 35 μm to 41 μm, such as from 36 μm to 40 μm, or from 37 μm to 39 μm, where particle size is determined by sieve analysis or by laser diffraction.

Un-milled crystalline 4-((L-valyl)oxy)butanoic acid can have a uniformity from 0.45 to 0.65 such as from 0.50 to 0.60, wherein uniformity is determined using laser diffraction.

Un-milled crystalline 4-((L-valyl)oxy)butanoic acid can have a surface area of 270 $m^2/kg$ to 310 $m^2/kg$, such as from 280 $m^2/kg$ to 300 $m^2/kg$, wherein the surface area is determined using laser diffraction.

Un-milled crystalline 4-((L-valyl)oxy)butanoic acid can have a bulk density, for example, from 0.15 g/mL to 0.25 g/mL, such as from 0.18 g/mL to 0.22 g/mL, wherein the bulk density is determined according to USP 616, Method 1.

Un-milled crystalline 4-((L-valyl)oxy)butanoic acid can have a Hausner ratio, for example, from 1.65 to 1.95, or from 1.70 to 1.90, or from 1.75 to 1.85, wherein the Hausner ratio is determined according to USP 1174.

Milled crystalline 4-((L-valyl)oxy)butanoic acid can have a particle size distribution characterized by a D10 of 11.8 μm, a D50 of 5.6 μm, and a D90 of 10.6 μm, where particle size is determined by sieve analysis or by laser diffraction.

Milled crystalline 4-((L-valyl)oxy)butanoic acid can have a particle size distribution characterized by a D10 from 1 μm to 5 μm, a D50 of 4 μm to 8 μm, and a D90 of 10 μm to 14 μm, where particle size is determined by sieve analysis or by laser diffraction.

Milled crystalline 4-((L-valyl)oxy)butanoic acid can have a particle size distribution characterized by a D[4,3] from 12 μm to 22 μm such as from 14 μm to 20 μm, or from 16 μm to 18 μm, where particle size is determined by sieve analysis or by laser diffraction.

Milled crystalline 4-((L-valyl)oxy)butanoic acid can have a uniformity from 0.2 to 0.6 such as from 0.3 to 0.5, wherein uniformity is determined by laser diffraction.

Milled crystalline 4-((L-valyl)oxy)butanoic acid can have a surface area of 430 $m^2/kg$ to 630 $m^2/kg$, such as from 450 $m^2/kg$ to 610 $m^2/kg$, or from 470 $m^2/kg$ to 490 $m^2/kg$, wherein surface area is determined using laser diffraction.

Milled crystalline 4-((L-valyl)oxy)butanoic acid can have a bulk density, for example, from 0.10 g/mL to 0.14 g/mL, such as from 0.11 g/mL to 0.13 g/mL, wherein bulk density is determined according to USP 616, Method 1.

Milled crystalline 4-((L-valyl)oxy)butanoic acid can have a Hausner ratio, for example, from 1.6 to 1.8 or from 1.65 to 1.75, wherein the Hausner ratio is determined according to USP 1174.

Methods of synthesizing 4-((L-valyl)oxy)butanoic acid and properties of 4-((L-valyl)oxy)butanoic acid are disclosed, for example, in U.S. Pat. Nos. 10,457,627 and 11,279,669, each of which is incorporated by reference in its entirety.

Methods of synthesizing 4-((L-valyl)oxy)butanoic acid and properties of 4-((L-valyl)oxy)butanoic acid are also disclosed in Examples 1 and 2.

For example, 4-((L-valyl)oxy)butanoic acid can be prepared by (a) contacting benzyl bromide with butyrolactone to provide benzyl 4-hydroxybutanoate (2a); (b) contacting benzyl 4-hydroxybutanoate (2a) with carbobenzyloxy-L-valine to provide 4-(benzoyloxy)-4-oxobutyl((benzoyloxy)carbonyl)-L-valinate (2b); and (c) deprotecting 4-(benzoyloxy)-4-oxobutyl((benzoyloxy)carbonyl)-L-valinate (2b) to provide 4-((L-valyl)oxy)butanoic acid.

Alternatively, 4-((L-valyl)oxy)butanoic acid can be prepared according to the method shown in Scheme 1:

Scheme 1

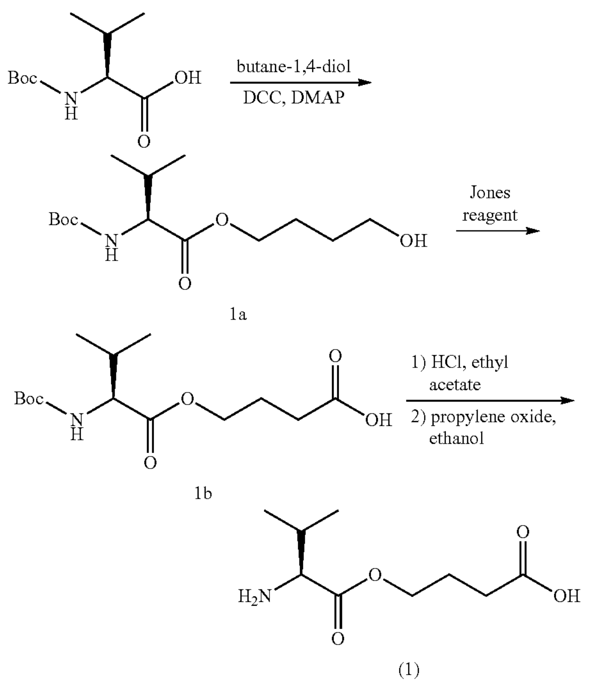

Boc-L-valine may be coupled to butane-1,4-diol to provide (S)-4-hydroxybutyl 2-(tert-butoxycarbonylamino)-3-methylbutanoate (1a) using a peptide coupling reagent, such as N,N'-dicyclohexylcarbodiimide (DCC), BOP, DEPBT, N,N'-diisopropylcarbodiimide (DIC), 1-ethyl-3-(3-dimethylaminopropyl)carbodiimide (EDCI), 4-(4,6-dimethoxy-1,3,5-triazin-2-yl)-4-methylmorpholinium chloride (DMTMM), HATU, HBTU, TBTU, PyAOP, PyBOP, 1,1'-thiocarbonyldiimdazole (TCDI), or 1,1'-carbonyldiimidazole (CDI). 1-Hydroxybenzotriazole (HOBt) or 1-hydroxy-7-aza-benzotriazole (HOAt) can be included to suppress racemization.

(S)-4-Hydroxybutyl 2-(tert-butoxycarbonylamino)-3-methylbutanoate (1a) can be treated with an oxidizer to provide (S)-4-(2-(tert-butoxycarbonylamino)-3-methylbutanoyloxy)butanoic acid (1b). Examples of suitable oxidizers include Jones reagent, potassium permanganate, ruthenium tetroxide, pyridinium dichromate in dimethylformamide (DMF), tetrapropylammonium perruthenate, or catalytic tetrapropylammonium perruthenate with stoichiometric N-methylmorpholine N-oxide. An alcohol can be oxidized to the aldehyde, such as with Dess-Martin periodinane, and subsequently oxidized to the carboxylic acid, such as with sodium chlorite.

(S)-4-(2-(tert-Butoxycarbonylamino)-3-methylbutanoyloxy)butanoic acid (1b) can be treated with an acid to provide the salt form of compound (1b). Examples of suitable acids include HCl, HCl in ethyl acetate, aqueous HCl, HCl in 1,4-dioxane, and trifluoroacetic acid. The salt form of compound (1b) can be neutralized with an acid scavenger to furnish the free amine form of 4-((L-valyl)oxy) butanoic acid. Examples of suitable acid scavengers include propylene oxide, an organic base, an amine base, an inorganic base, a carbonate salt, or a hydroxide salt.

4-((L-Valyl)oxy)butanoic acid can alternatively be prepared according to the method summarized in Scheme 2:

Scheme 2

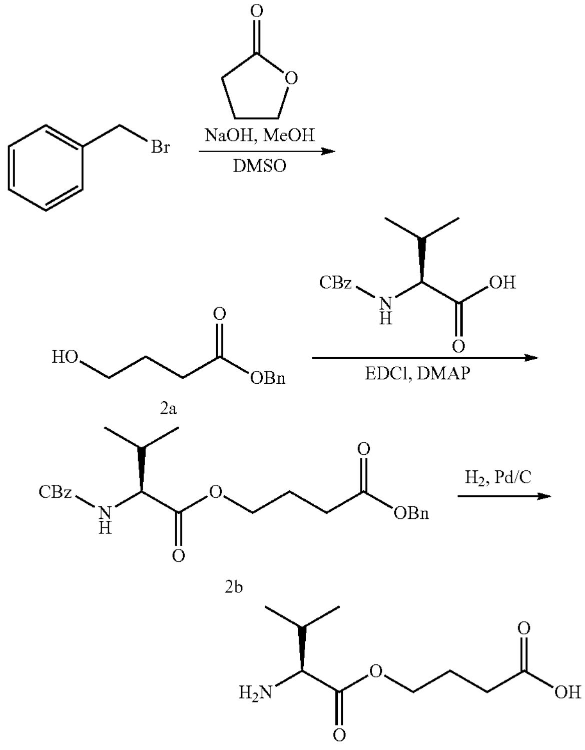

2a

2b

1

Benzyl 4-hydroxybutanoate (2a) can be prepared from the ring-opening hydrolysis and subsequent benzylation of γ-butyrolactone. Alternatively, benzyl 4-hydroxybutanoate (2a) can be purchased commercially.

CBz-L-valine can be coupled to benzyl 4-hydroxybutanoate (2a) to provide 4-(benzyloxy)-4-oxobutyl(benzyloxy) carbonyl)-L-valinate (2b) using a peptide coupling reagent, such as, for example, DCC, BOP, DEPBT, DIC, EDCI, DMTMM, HATU, HBTU, TBTU, PyAOP, PyBOP, TCDI, or CDI. 1-Hydroxybenzotriazole (HOBt) or 1-hydroxy-7-aza-benzotriazole (HOAt) can be included in the reaction to suppress racemization.

4-(Benzyloxy)-4-oxobutyl(benzyloxy)carbonyl)-L-valinate (2b) can be hydrogenated in the presence of hydrogen gas and a catalyst derived from a metal such as palladium, platinum, ruthenium, nickel, rhodium, or iridium to provide 4-((L-valyl)oxy)butanoic acid.

Crystalline 4-((L-valyl)oxy)butanoic acid can be prepared by (i) dissolving 4-((L-valyl)oxy)butanoic acid in a first solvent to obtain a solution; and (ii) crystallizing the solution to obtain crystalline 4-((L-valyl)oxy)butanoic acid.

The first solvent can comprise, for example, methanol, ethanol, isopropanol, tetrahydrofuran, ethyl acetate, acetone, isobutanol, isopropyl acetate, acetonitrile, 2-butanone, toluene, water, tert-butyl methyl ether, n-propanol, isopentanol, butyl acetate, ethyl formate, methyl acetate, isobutyl acetate, n-heptane, dichloromethane, 1,4-dioxane, cyclohexane, xylene, 4-methyl-2-pentanone, ethyl ether, or a combination of any of the foregoing.

4-((L-Valyl)oxy)butanoic acid can be dissolved in the solvent at a temperature, for example, from 60° C. to 90° C., from 65° C. to 85° C., or from 70° C. to 80° C.

After dissolving 4-((L-valyl)oxy)butanoic acid in a first solvent, a second solvent can be added to the solution. For example, the second solvent can comprise acetonitrile, tetrahydrofuran, isopropanol, acetone, ethyl acetate, tert-butyl methyl ether, 1,4-dioxane, or a combination of any of the foregoing.

Crystallizing 4-((L-valyl)oxy)butanoic acid can comprise, for example, heating the solution to a temperature from 60° C. to 90° C., such as from 65° C. to 85° C., or from 60° C. to 80° C., and maintaining the solution at this temperature, for example, from 0.5 hours to 2 hours.

Crystallizing can further comprise cooling the heated solution, for example, to a temperature from 20° C. to 25° C.

The crystallized 4-((L-valyl)oxy)butanoic acid can be filtered and washed to provide crystalline 4-((L-valyl)oxy) butanoic acid.

Crystalline 4-((L-valyl)oxy)butanoic acid can be recrystallized, for example, by warming a solvent, adding crystalline 4-((L-valyl)oxy)butanoic acid to the solvent, and dissolving the crystalline 4-((L-valyl)oxy)butanoic acid in the solvent. The solvent can be, for example, ethanol, 50:1 ethanol/water, water, methanol, or isopropanol. Additional solvent can be added and/or optionally a suitable amount of an anti-solvent can be added to the clear solution. Examples of suitable anti-solvent include acetone ethyl acetate and methyl tert-butyl ether. For example, the volume ratio of methanol to methyl tert-butyl ether can be bout 1:3. After the solution is stirred for about 30 minutes, the solution can be cooled to a temperature from 20° C. to 25° C. and filtered to provide crystalline 4-((L-valyl)oxy)butanoic acid as a solid precipitate.

Crystalline 4-((L-valyl)oxy)butanoic acid can be incorporated into a pharmaceutical composition to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. A pharmaceutical composition provided by the present disclosure can be an injectable intravenous formulation. A pharmaceutical composition provided by the present disclosure can be an oral formulation. An oral formulation can be an oral dosage form.

Pharmaceutical compositions provided by the present disclosure can comprise a therapeutically effective amount of crystalline 4-((L-valyl)oxy)butanoic acid together with a suitable amount of one or more pharmaceutically acceptable vehicles so as to provide a composition for proper administration to a patient. Suitable pharmaceutical vehicles and methods of preparing pharmaceutical compositions are described in the art.

A pharmaceutical composition provided by the present disclosure can provide a therapeutically effective amount of γ-hydroxybutyric acid in the systemic circulation of a patient following administration to the patient, such as following oral administration to the patient.

Accordingly, it is within the capability of those of skill in the art to assay and use crystalline 4-((L-valyl)oxy)butanoic acid and/or pharmaceutical compositions thereof for therapy.

Crystalline 4-((L-valyl)oxy)butanoic acid and/or a pharmaceutical composition thereof can be used in an amount effective to achieve the intended purpose. For example, crystalline 4-((L-valyl)oxy)butanoic acid or pharmaceutical composition thereof can be administered to a patient in a therapeutically effective amount to treat a disease or symptom of a disease such as a sleep disorder.

The amount of crystalline 4-((L-valyl)oxy)butanoic acid and/or pharmaceutical composition thereof that will be effective in the treatment of a particular disorder or can depend in part on the nature of the disorder or condition, and can be determined by standard clinical techniques known in the art. In addition, in vitro or in vivo assays may optionally be employed to help identify optimal dosage ranges. A suitable amount of crystalline 4-((L-valyl)oxy)butanoic acid and/or a pharmaceutical composition thereof administered can depend on, among other factors, the patient being treated, the weight of the patient, the severity of the affliction, the manner of administration and the judgment of the prescribing physician.

Crystalline 4-((L-valyl)oxy)butanoic acid can be assayed in vitro and in vivo, for the desired therapeutic activity, prior to use in humans. Crystalline 4-((L-valyl)oxy)butanoic acid can also be demonstrated to be effective and safe using animal model systems.

In certain embodiments, a therapeutically effective dose of crystalline 4-((L-valyl)oxy)butanoic acid and/or pharmaceutical composition thereof can provide therapeutic benefit without causing substantial toxicity. Toxicity of crystalline 4-((L-valyl)oxy)butanoic acid and/or a pharmaceutical composition thereof can be determined using standard pharmaceutical procedures and may be ascertained by one skilled in the art. The dose ratio between toxic and therapeutic effect is the therapeutic index. A compound of crystalline 4-((L-valyl)oxy)butanoic acid and/or a pharmaceutical composition thereof can exhibit a high therapeutic index in treating a disease and disorder. A dose of crystalline 4-((L-valyl)oxy)butanoic acid and/or pharmaceutical composition thereof can be within a range of circulating concentrations that include an effective dose with minimal toxicity.

A pharmaceutical composition provided by the present disclosure can further comprise one or more pharmaceutically active compounds in addition to crystalline 4-((L-valyl)oxy)butanoic acid. Such compounds can be provided to treat the disease being treated with the compound of Formula or to treat a disease, disorder, or condition other than that being treated with crystalline 4-((L-valyl)oxy)butanoic acid.

Crystalline 4-((L-valyl)oxy)butanoic acid or a pharmaceutical composition thereof can be used in combination with at least one other therapeutic agent. Crystalline 4-((L-valyl)oxy)butanoic acid or a pharmaceutical composition thereof may be administered to a patient together with another compound for treating a disease such as a sleep disorder in the patient. Crystalline 4-((L-valyl)oxy)butanoic acid and the at least one other therapeutic agent can act additively or synergistically. The at least one additional therapeutic agent can be included in the same pharmaceutical composition or vehicle comprising crystalline 4-((L-valyl)oxy)butanoic acid or can be in a separate pharmaceutical composition or vehicle. Accordingly, methods provided by the present disclosure further include, in addition to administering crystalline 4-((L-valyl)oxy)butanoic acid, administering one or more therapeutic agents effective for treating a different disease, disorder or condition other than the disease being treated with γ-hydroxybutyric acid. Methods provided by the present disclosure include administering crystalline 4-((L-valyl)oxy)butanoic acid or a pharmaceutical composition thereof and one or more other therapeutic agents provided that the combined administration does not inhibit the therapeutic efficacy of crystalline 4-((L-valyl)oxy)butanoic acid and/or γ-hydroxybutyric acid and/or does not produce adverse combination effects.

A pharmaceutical composition comprising crystalline 4-((L-valyl)oxy)butanoic acid can be administered concurrently with the administration of another therapeutic agent, which may be part of the same pharmaceutical composition as, or in a different pharmaceutical composition than that comprising crystalline 4-((L-valyl)oxy)butanoic acid. Crystalline 4-((L-valyl)oxy)butanoic acid or a pharmaceutical composition thereof may be administered prior or subsequent to administration of another therapeutic agent. In certain embodiments of combination therapy, the combination therapy may comprise alternating between administering crystalline 4-((L-valyl)oxy)butanoic acid and a pharmaceutical composition comprising another therapeutic agent such as to minimize adverse drug effects associated with a particular drug. When crystalline 4-((L-valyl)oxy)butanoic acid is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising crystalline 4-((L-valyl)oxy)butanoic acid may be administered with one or more substances, for example, to enhance, modulate and/or control release, bioavailability, therapeutic efficacy, therapeutic potency, and/or stability of crystalline 4-((L-valyl)oxy)butanoic acid. For example, to enhance the therapeutic efficacy of crystalline 4-((L-valyl)oxy)butanoic acid or a pharmaceutical composition comprising crystalline 4-((L-valyl)oxy)butanoic acid may be co-administered with one or more active agents to increase the absorption or diffusion and/or transport of the compound of Formula from the gastrointestinal tract into the systemic circulation, or to inhibit degradation of crystalline 4-((L-valyl)oxy)butanoic acid in the blood of a patient. A pharmaceutical composition comprising crystalline 4-((L-valyl)oxy)butanoic acid may be co-administered with an active agent having pharmacological effects that enhance the therapeutic effectiveness of the compound of Formula or the therapeutic efficacy of γ-hydroxybutyric acid.

For oral therapeutic administration, crystalline 4-((L-valyl)oxy)butanoic acid can be incorporated with excipients and used, for example, in the form of tablets, buccal tablets or tabs, troches, capsules, elixirs, suspensions, syrups, or wafers, to be admixed with an aqueous medium. A dosage form can comprise a therapeutically effective amount of crystalline 4-((L-valyl)oxy)butanoic acid or less than a therapeutically effective amount of crystalline 4-((L-valyl)oxy)butanoic acid.

An oral formulation such as an oral dosage form can contain, for example, from 1 gram to 18 grams of crystalline 4-((L-valyl)oxy)butanoic acid.

An oral formulation such as an oral dosage form can contain, for example, from 0.5 gram-equivalents to 9 gram-equivalents of γ-hydroxybutyric acid.

An oral dosage form such as a granulation, tablet, troche, pill, capsule, or suspension, can also contain, for example, a binder, natural as gum tragacanth, acacia, cornstarch, or gelatin or synthetic as polyvinyl acetate; excipients, such as dicalcium phosphate; a disintegrating agent, such as corn starch, potato starch, or alginic acid; a lubricant, such as magnesium stearate; and a sweetening agent, such as, lactose or saccharin may be added or a natural or synthetic flavoring agent. When a dosage form is a capsule for admixing with a specific volume of an aqueous medium, a dosage form can contain a liquid carrier. Various other materials can be present as coatings or to otherwise modify the physical form of the dosage unit. For instance, tablets, pills, or capsules can be coated with sugar, natural or synthetic polymers, or a combination of any of the foregoing.

An oral dosage form can comprise a granulation, wherein the granulation comprises granules comprising crystalline 4-((L-valyl)oxy)butanoic acid. The granulation can comprise immediate release granules comprising crystalline 4-((L-valyl)oxy)butanoic acid, modified release granules comprising crystalline 4-((L-valyl)oxy)butanoic acid, or a combination thereof.

Granules can comprise a core comprising crystalline 4-((L-valyl)oxy)butanoic acid and optionally a coating surrounding the core. The coating can be, for example, a seal coating or a modified release coating. Granules comprising an uncoated core are referred to as an uncoated granulation.

An uncoated granulation of crystalline 4-((L-valyl)oxy)butanoic acid can be characterized, for example, by an average particle size from 50 μm to 600 μm, from 100 μm to 550 μm, from 100 μm to 500 μm, from 150 μm to 500 μm, from 200 μm to 500 μm, from 250 μm to 450 μm, or from 200 μm to 400 μm, where the average particle size is determined by sieve analysis or by laser diffraction.

An uncoated granule can comprise a high loading of crystalline 4-((L-valyl)oxy)butanoic acid. For example, an uncoated granule can comprise greater than 80 wt %, greater than 85 wt %, greater than 90 wt %, greater than 95 wt %, greater than 96 wt %, greater than 97 wt %, greater than 98 wt %, or greater than 99 wt % of crystalline 4-((L-valyl)oxy)butanoic acid, where wt % is based on the total weight of the uncoated granule. An uncoated granule can comprise, for example, from 80 wt % to 99.5 wt % of crystalline 4-((L-valyl)oxy)butanoic acid, from 85 wt % to 95 wt %, from 87 wt % to 93 wt %, or from 88 wt % to 92 wt % of crystalline 4-((L-valyl)oxy)butanoic acid, where wt % is based on the total weight of the uncoated granule. An uncoated granule can comprise, for example, from 85 wt % to 95 wt % of crystalline 4-((L-valyl)oxy)butanoic acid, from 86 wt % to 94 wt %, from 87 wt % to 93 wt %, or from 88 wt % to 92 wt % of crystalline 4-((L-valyl)oxy)butanoic acid, where wt % is based on the total weight of the uncoated granule.

An uncoated granule or granulation can comprise, for example, from 80 wt % to 99 wt % of crystalline 4-((L-valyl)oxy)butanoic acid, from 1 wt % to 10 wt % of an antistatic agent such as hydrated magnesium silicate (talc), and from 1 wt % to 10 wt % of a water-soluble polymer such as hydroxypropylmethyl cellulose, where wt % is based on the total weight of the granule or granulation. An uncoated granule or granulation can comprise, for example, from 85 wt % to 95 wt % of crystalline 4-((L-valyl)oxy)butanoic acid, from 2 wt % to 8 wt % of an antistatic agent such as hydrated magnesium silicate (talc), and from 2 wt % to 8 wt % of a water-soluble polymer such as hydroxypropylmethyl cellulose, where wt % is based on the total weight of the granule or granulation. An uncoated granule or granulation provided by the present disclosure can comprise, for example, from 87 wt % to 93 wt % of crystalline 4-((L-valyl)oxy)butanoic acid, from 3 wt % to 7 wt % of an antistatic agent such as hydrated magnesium silicate (talc), and from 3 wt % to 7 wt % of a water-soluble polymer such as hydroxypropylmethyl cellulose, where wt % is based on the total weight of the granule or granulation.

An uncoated granule or granulation can be characterized by an average sphericity, for example, from 0.90 to 1, such as from 0.91 to 0.99, or from 0.92 to 0.98, where sphericity is determined using wet dispersion particle shape methods or by dynamic image analysis. An uncoated granule or granulation can be characterized by an average sphericity, for example, greater than 0.90, greater than 0.91, greater than 0.92, greater than 0.93, greater than 0.94, or greater than 0.95.

Uncoated granules are solid and are characterized by a substantially homogeneous composition throughout the granule.

Uncoated granules provided by the present disclosure can be characterized by a sphericity, for example, from 0.90 to 1, such as from 0.91 to 0.99, or from 0.92 to 0.98, where sphericity is determined using wet dispersion particle shape methods or by dynamic image analysis. A granulation provided by the present disclosure can be characterized by an average sphericity, for example, greater than 0.90, greater than 0.91, greater than 0.92, greater than 0.93, greater than 0.94, or greater than 0.95. A granulation provided by the present disclosure can comprise a plurality of granules characterized by an average sphericity, for example, greater than 0.94, greater than 0.95, greater than 0.96, greater than 0.97, greater than 0.98, or greater than 0.99.

Uncoated granules provided by the present disclosure are solid and are characterized by a substantially homogeneous composition throughout the granule.

An uncoated granulation can have a bulk density, for example, greater than 0.40 g/mL, greater than 0.50 g/mL, greater than 0.60 g/mL, greater than 0.90 g/mL, greater than 1.10 g/mL, greater than 1.30 g/mL, or greater than 1.50 g/mL.

An uncoated granulation can have a bulk density, for example, from 0.40 g/mL to 1.60 g/mL, from 0.40 g/mL to 1.20 g/mL, from 0.40 g/mL to 0.80 g/mL, from 0.50 g/mL to 1.60 g/mL, from 0.50 g/mL to 1.40 g/mL, from 0.50 g/mL to 1.20 g/mL, from 0.60 g/mL to 1.60 g/mL, from 0.70 g/mL to 1.50 g/mL, from 0.80 g/mL to 1.40 g/mL, or from 1.00 g/mL to 1.20 g/mL. A granulation can have a bulk density, for example, from 0.5 g/mL to 0.8 g/mL, from 0.55 g/mL to 0.75 g/mL, or from 0.6 g/mL to 0.7 g/mL.

Bulk density can be determined using a bulk density cylinder.

Uncoated granules provided by the present disclosure have smooth surfaces. Smooth granule surfaces facilitate the ability to coat the granules with a thin, continuous coating having a substantially homogeneous thickness. The qualities of the coating can be important for controlled release formulations. For example, rough and/or porous surfaces tend to require a significantly higher amount of coating to achieve a comparable release profile to smooth surfaces. In addition, coatings of rough and/or porous surfaces can lead to variable dissolution or release profile.

An uncoated granulation provided by the present disclosure, when dried, can be characterized by a loss on drying (LOD), for example, from 0.05 wt % to 1.5 wt %, from 0.1 wt % to 1.4 wt %, from 0.2 wt % to 1.2 wt %, from 0.2 wt % to 1.3 wt %, from 0.3 wt % to 1.2 wt %, from 0.7 wt % to 1.1 wt %, from 0.92 wt % to 0.98 wt %, from 0.93 wt % to 0.97 wt %, or from 0.94 wt % to 0.96 wt %, where wt % is based on the total weight of the granulation. A granulation provided by the present disclosure, when dried, can be characterized by a loss on drying (LOD), for example, of less than 1.5 wt %, less than 1.3 wt %, less than 1.1 wt %, less than 0.9 wt %, less than 0.7 wt %, less than 0.5 wt %, or less than 0.1 wt %, where wt % is based on the total weight of the granulation. The LOD represents removal of water incorporated into the granules during preparation of the granulation and after drying.

LOD is determined by thermogravimetric analysis.

An uncoated granulation provided by the present disclosure can be characterized by a friability value, for example, from 0 wt % to 2 wt % such as less than 2 wt %, less than 1.5 wt %, less than 1 wt %, or less than 0.5 wt %, where wt % is based on the total weight of the granulation. A granulation provided by the present disclosure can be characterized by a friability value, for example, from 0.1 wt % to 2 wt %, from 0.2 wt % to 1.8 wt %, from 0.2 wt % to 1.6 wt %, from 0.4 wt % to 1.2 wt %, or from 0.6 wt % to 1.2 wt %, where wt % is based on the total weight of the granulation. Granules with low friability are easier to coat than are granules with high friability. Friability is defined as the amount (wt %) of granules having a diameter less than 75 μm that are generated by subjecting a granulation to a sonic sifter operated at a vibration amplitude of 8 corresponding to 3,600 sonic energy pulses per minute for at least 2 minutes.

An uncoated granulation provided by the present disclosure can have a friability, for example, of less than 1.02% where friability is determined using a sonic sifter.

Uncoated granules comprising crystalline 4-((L-valyl) oxy)butanoic acid can be prepared using MicroPX® micropelletizing technology (Glatt GmbH).

Uncoated granules comprising crystalline 4-((L-valyl) oxy)butanoic acid can be prepared by a combination of dry granulation and wet granulation.

Crystalline 4-((L-valyl)oxy)butanoic acid can be screened, de-lumped, co-milled, Fitz-milled, pin-milled, or jet-milled before adding to the dry mixture.

Crystalline 4-((L-valyl)oxy)butanoic acid can have a size distribution characterized by a D90, for example, less than 30 μm, less than 25 μm, less than 20 μm, or less than 15 μm. An active pharmaceutical ingredient can have a size distribution characterized by a D90, for example, from 10 μm to 30 μm, from 11 μm to 25 μm, or from 10 μm to 20 μm. An as-crystallized active pharmaceutical ingredient can be jet-milled to provide a suitable particle size distribution.

The dry mixture can be mixed in a bowl, for example, for from 0.5 minutes to 5 minutes to provide a homogeneous dry mixture.

Granulating can comprise the steps of (a) granulating the dry mixture to provide a dry granulation; and (b) adding water to the dry granulation and granulating to provide a wet granulation.

A granulation can comprise an immediate release granulation.

An immediate release granulation can comprise a plurality of uncoated granules or a plurality of granules comprising a seal coating.

A seal coating can comprise a water-soluble polymer such as hydroxypropyl cellulose, hydroxypropylmethyl cellulose or any of the water-soluble polymers disclosed herein.

A seal coating can comprise an antistatic agent such as talc, magnesium stearate, or a combination thereof.

A seal coating can comprise, for example, from 65 wt % to 95 wt % of a water-soluble polymer, such as from 70 wt % to 90 wt %, or from 75 wt % to 85 wt % of a water-soluble polymer; and from 5 wt % to 35 wt % of an antistatic agent, such as from 10 wt % to 30 wt %, or from 15 wt % to 25 wt % if an antistatic agent where wt % is based on the total weight of the seal coating.

A seal coating can have a thickness, for example, from 0.5 μm to 4 μm, from 1 μm to 3.5 μm, from 1 μm to 3 μm, or from 1 μm, to 2.5 μm.

An immediate release granulation comprising a plurality of uncoated or seal-coated granules can comprise, for example, greater than 80 wt % such as from 85 wt % to 95 wt % of crystalline 4-((L-valyl)oxy)butanoic acid. An immediate release granulation comprising uncoated or seal-coated granules can dissolve completely, for example, in less than 10 minutes, less than 8 minutes, less than 6 minutes, less than 5 minutes, or less than 4 minutes, when tested in a USP Type 2 dissolution apparatus in an aqueous buffered solution at pH 4.5 at a temperature of 37° C. and a paddle speed of 100 rpm.

An immediate release granulation can comprise a plurality of coated or seal-coated granules having an immediate release functional coating. An immediate release granulation comprising a plurality of coated granules can comprise greater than 80 wt % of crystalline 4-((L-valyl)oxy)butanoic acid. An immediate release granulation comprising coated granules can dissolve completely, for example, in less than 25 minutes, less than 20 minutes, less than 18 minutes, less than 16 minutes, less than 14 minutes, or less than 12 minutes, when tested in a USP Type 2 dissolution apparatus in a buffered solution at pH 4.5 at a temperature of 37° C. and a paddle speed of 100 rpm. An immediate release granulation comprising coated granules can release greater than 80% of crystalline 4-((L-valyl)oxy)butanoic acid, for example, in less than 10 minutes, less than 8 minutes, less than 6 minutes, or less than 4 minutes, when tested in a USP Type 2 dissolution apparatus in a buffered solution at pH 4.5 at a temperature of 37° C. and a paddle speed of 100 rpm. A coated immediate release granulation can comprise a coating comprising a water-soluble-polymer such as, for example, hydroxypropylcellulose, polyvinyl alcohol, hydroxypropylmethyl cellulose, hydroxypropylethyl cellulose, polyvinylpyrrolidone, or polyethylene glycol. A coated immediate release granulation can comprise a coating comprising an antistatic agent such as talc, magnesium stearate, or silicon dioxide.

A modified release granulation can comprise a plurality of granules coated with a functional coating. A functional coating can comprise, for example, a modified release coating such as a controlled release coating, a sustained release coating, a pH-release coating, a pulsatile release coating, a timed-release coating, or a delayed release coating. A functional coating can be configured to release crystalline 4-((L-valyl)oxy)butanoic acid from a coated granule, for example, over an intended period of time following ingestion and/or in an intended region of the gastrointestinal tract.

A modified release granule can comprise an uncoated granule comprising crystalline 4-((L-valyl)oxy)butanoic acid with one or more functional coatings surrounding the uncoated granule.

Each of the one or more functional coatings can independently have an average thickness, for example, of less than 50 μm, less than 40 μm, less than 30 μm, less than 20 μm, less than 15 μm, less than 10 μm, or less than 5 μm. Each of the one or more functional coatings can independently have an average thickness, for example, from 5 μm to 50 μm, from 5 μm to 40 μm, from 5 μm to 30 μm, from 5 μm to 20 μm, from 5 μm to 15 μm, or from 5 μm to 10 μm.

A coated granule or coated granulation can comprise, for example, greater than 50 wt % of crystalline 4-((L-valyl)oxy)butanoic acid, greater than 55 wt %, greater than 60 wt %, greater than 70 wt %, greater than 70 wt %, greater than 80 wt %, or greater than 85 wt % of crystalline 4-((L-valyl)oxy)butanoic acid, where wt % is based on the total weight of the coated granule or coated granulation.

A coated granule or coated granulation comprising a plurality of coated granules can comprise, for example, from 50 wt % to 90 wt % of crystalline 4-((L-valyl)oxy)butanoic acid, from 60 wt % to 90 wt %, from 70 wt % to 90 wt %, from 75 wt % to 85 wt %, or from 77 wt % to 83 wt % of crystalline 4-((L-valyl)oxy)butanoic acid, where wt % is based on the total weight of the coated granule or coated granulation.

A coated granule or coated granulation can comprise, for example, less than 50 wt % of a functional coating, less than 40 wt % of a functional coating, less than 30 wt %, less than 20 wt %, or less than 10 wt % of a functional coating, where wt % is based on the total weight of the coated granule or coated granulation. A coated granule or coated granulation can comprise, for example, from 10 wt % to 50 wt % of a functional coating, from 10 wt % to 45 wt %, from 15 wt % to 40 wt %, or from 15 wt % to 35 wt % of a functional coating, wherein wt % is based on the total weight of the coated granulation. Coated granulations comprising crystalline 4-((L-valyl)oxy)butanoic acid can have a thick coating to reduce the release rate of crystalline 4-((L-valyl)oxy)butanoic acid and/or increase the storage stability of crystalline 4-((L-valyl)oxy)butanoic acid by minimizing or preventing ingress of moisture.

A functional coating can comprise a time release coating the releases the crystalline 4-((L-valyl)oxy)butanoic acid with time in an aqueous environment. The release of crystalline 4-((L-valyl)oxy)butanoic acid can be characterized by a zero-order release profile.

A functional coating can comprise a matrix polymer or combination of matrix polymers. A combination of a matrix polymer and/or a pore forming polymer can be selected to provide for a desired release profile of crystalline 4-((L-valyl)oxy)butanoic acid in the gastrointestinal tract.

A functional coating can comprise, for example, from 55 wt % to 95 wt % of a matrix polymer, from 60 wt % to 90 wt %, from 65 wt % to 90 wt %, from 70 wt % to 85 wt %, or from 75 wt % to 85 wt %, of a matrix polymer, where wt % is based on the total weight of the functional coating.

A functional coating can comprise a matrix polymer or combination of matrix polymers. A combination of a matrix polymer can be selected to provide for a desired release profile of 4-((L-valyl)oxy)butanoic acid in the gastrointestinal tract.

A functional coating can comprise, for example, from 55 wt % to 95 wt % of a matrix polymer, from 60 wt % to 90 wt %, from 65 wt % to 90 wt %, from 70 wt % to 85 wt %, or from 75 wt % to 85 wt %, of a matrix polymer, where wt % is based on the total weight of the functional coating.

A functional coating can comprise, for example less than 95 wt % of a matrix polymer, less than 90 wt %, less than 85 wt %, less than 80 wt %, less than 75 wt %, less than 70 wt %, or less than 60 wt % of a matrix polymer, where wt % is based on the total weight of the functional coating.

A functional coating can comprise, for example, greater than 50% of a matrix polymer, great than 55 wt %, greater than 60 wt %, greater than 65 wt %, greater than 70 wt %, greater than 75 wt %, greater than 80 wt %, greater than 85 wt %, or greater than 90 wt % of a matrix polymer, where wt % is based on the total weight of the functional coating.

A matrix polymer can comprise a water-insoluble polymer or combination of water-insoluble polymers.

Examples of suitable water-insoluble polymers include ethylcellulose, polyvinyl acetates, polyacrylates, and polymethacrylates.

A water-insoluble polymer such as ethylcellulose can have an average molecular weight, for example, from 25,000 Daltons to 300,000 Daltons, such as from 50,000 Daltons to 200,000 Daltons, from 50,000 Daltons to 150,000 Daltons, or from 50,000 Daltons to 100,000 Daltons.

A water-insoluble polymer such as ethylcellulose can have a viscosity, for example, less than 100 mPa×sec, less than 75 mPa×sec, less than 50 mPa×sec, less than 25 mPa×sec, less than 20 mPa×sec, or less than 15 mPa×sec, as determined using a Brookfield viscometer in an 80:20 mixture of toluene/ethanol.

Examples of suitable ethylcellulose polymers include Aqualon® T10 Pharm, N7 Pharm, N10 Pharm, N14 Pharm, N22 Pharm, N50 Pharm, and N100 Pharm polymers, available from Ashland. Other examples of suitable ethylcellulose polymers include Ethocel® Standard 7, Standard 10, Standard 14, Standard 20 polymers, available from Dupont.

A matrix polymer can comprise, for example, from 90 wt % to 100 wt % of a water-insoluble polymer, from 91 wt % to 99 wt %, from 82 wt % to 98 wt %, or from 93 wt % to 97 wt % of a water-insoluble polymer, where wt % is based on the total weight of the matrix polymer. A matrix polymer can comprise, for example, greater than 90 wt % of a water-insoluble polymer, greater than 92 wt %, greater than 94 wt %, greater than 96 wt %, or greater than 98 wt % of a water-insoluble polymer, where wt % is based on the total weight of the matrix polymer. A matrix polymer can comprise, for example less than 100 wt % of a water-insoluble polymer, less than 98 wt %, less than 96 wt %, less than 94 wt %, or less than 92 wt % of a water-insoluble polymer, where wt % is based on the total weight of the matrix polymer.

A matrix polymer can comprise a pore forming polymer. Examples of pore forming polymers include water-soluble polymers, polymers that swell or expand such as carbomers, and polymers soluble in gastric fluid such as cellulose acetate phthalate, hydroxypropyl cellulose, hydroxypropylmethyl cellulose, methacrylic acid-methyl methacrylate copolymers, and polyvinyl acetate phthalate. A pore forming polymer can increase the permeability of a functional coating under intended conditions.

A matrix polymer can comprise a water-soluble polymer or combination of water-soluble polymers.

Examples of suitable water-soluble polymers include hydroxypropyl cellulose, polyvinyl alcohol, hydroxypropylmethyl cellulose, hydroxypropylethyl cellulose, polyvinylpyrrolidone, polyethylene glycol, polyvinyl alcohol, povidone, copovidone, and poloxamer.

A water-soluble polymer such as hydroxypropyl cellulose can have an average molecular weight, for example, less than 1,000,000 Daltons, less than 800,000 Daltons, less than 600,000 Daltons, less than 400,000 Daltons, less than 200,000 Daltons, less than 100,000 Daltons, or less than 50,0000 Daltons.

A water-soluble polymer such as hydroxypropyl cellulose can have a viscosity, for example, less than 7,000 mPa×sec, less than 5,000 mPa×sec, less than 3,000 mPa×sec, or less than 1,000 mPa×sec, as determined using a Brookfield viscometer in an 80:20 mixture of toluene/ethanol.

Examples of suitable hydroxypropyl cellulose polymers include Klucel® HF Pharm, MF Pharm, GF Pharm JF Pharm, LF Pharm, EF Pharm, and ELF Pharm polymers, available from Ashland.

Examples of suitable hydroxypropylmethyl cellulose polymers include Pharmacoat® 603, 645, 606 and 615 polymers, available from Shin-Etsu Chemical Co.

A matrix polymer can comprise, for example, from 0 wt % to 15 wt % of a water-soluble polymer such as ethylcellulose, from 0 wt % to 10 wt %, from 1 wt % to 8 wt %, or from 2 wt % to 6 wt % of a water-soluble polymer, where wt % is based on the total weight of the matrix polymer. A matrix polymer can comprise, for example, greater than 0 wt % of a water-soluble polymer such as hydroxypropyl cellulose, greater than 2 wt %, greater than 4 wt %, greater than 6 wt %, or greater than 8 wt % of a water-soluble polymer, where wt % is based on the total weight of the matrix polymer. A matrix polymer can comprise, for example, less than 10 wt % of a water-soluble polymer, less than 8 wt %, less than 6 wt %, less than 4 wt %, or less than 2 wt % of a water-soluble polymer, where wt % is based on the total weight of the matrix polymer.

A matrix polymer can comprise, for example, from 90 wt % to 100 wt % of a water-insoluble polymer such as ethylcellulose and from 0 wt % to 10 wt % of a water-soluble polymer such as hydroxypropyl cellulose, from 92 wt % to 98 wt % of a water-insoluble polymer and from 2 wt % to 8 wt % of a water-soluble polymer, or from 94 wt % to 96 wt % of a water-insoluble polymer and from 4 wt % to 6 wt % of a water-soluble polymer, where wt % is based on the total weight of the matrix polymer.

A functional coating can be applied to granules provided by the present disclosure by any suitable method such as by spraying a solution, suspension, or dispersion of the functional coating onto granules in a fluidized bed apparatus.

In addition to a matrix polymer or combination of matrix polymers, a functional coating can comprise, for example, a plasticizing agent, an anti-static, an anti-tacking agent, a colorant or pigment, a glidant, a viscosity modifier, or a combination of any of the foregoing.

A functional coating can comprise an antistatic agent or combination of antistatic agents.

An antistatic agent is useful to minimize or prevent agglomeration of the granules during application of the functional coating.

Examples of suitable antistatic agents include talc (hydrated magnesium silicate), magnesium stearate, and silicon dioxide.

A functional coating can comprise, for example, from 5 wt % to 25 wt % of an antistatic agent, such as from 8 wt % to 22 wt %, or from 10 wt % to 20 wt % of an antistatic agent, where wt % is based on the total weight of the functional coating. A functional coating can comprise, for example, less than 25 wt % of an antistatic agent, less than 23 wt %, less than 18 wt %, or less than 15 wt % of an antistatic agent, where wt % is based on the total weight of the functional coating. A functional coating can comprise, for example, greater than 5 wt % of an antistatic agent, greater than 8 wt %, greater than 12 wt %, greater than 16 wt %, or greater than 20 wt % of an antistatic agent, where wt % is based on the total weight of the functional coating.

A functional coating provided by the present disclosure does not include a plasticizer such as dibutyl sebacate, polyethylene glycol, triacetin, and triethyl citrate.

A functional coating provided by the present disclosure can comprise, for example, from 70 wt % to 95 wt % of a matrix polymer and from 5 wt % to 30 wt % of an antistatic agent, where wt % is based on the total weight of the functional coating.

A functional coating provided by the present disclosure can comprise, for example, from 75 wt % to 90 wt % of a matrix polymer and from 10 wt % to 25 wt % of an antistatic agent, where wt % is based on the total weight of the functional coating.

A functional coating provided by the present disclosure can comprise, for example, from 80 wt % to 90 wt % of a matrix polymer and from 10 wt % to 12 wt % of an antistatic agent, where wt % is based on the total weight of the functional coating.

In a functional coating provided by the present disclosure, a matrix polymer can comprise ethylcellulose and hydroxypropyl cellulose, and the antistatic agent can comprise magnesium stearate, or hydrated magnesium silicate, or a combination thereof.

A functional coating such as a modified release coating of the present disclosure can comprise, for example, from 72 wt % to 92 wt % of a water-insoluble polymer such as ethyl cellulose, form 0.5 wt % to 4 wt % of a water-soluble polymer such as hydroxypropylmethyl cellulose, and from 11 wt % to 22 wt % of an antistatic agent such as magnesium stearate or hydrated magnesium silicate, where wt % is based on the total weight of the functional coating. A functional coating such as a modified release coating of the present disclosure can comprise, for example, from 74 wt % to 90 wt % of a water-insoluble polymer such as ethyl cellulose, form 1 wt % to 3.5 wt % of a water-soluble polymer such as hydroxypropylmethyl cellulose, and from 13 wt % to 20 wt % of an antistatic agent such as magnesium stearate or hydrated magnesium silicate, where wt % is based on the total weight of the functional coating. A functional coating such as a modified release coating of the present disclosure can comprise, for example, from 76 wt % to 88 wt % of a water-insoluble polymer such as ethyl cellulose, form 1 wt % to 3.0 wt % of a water-soluble polymer such as hydroxypropylmethyl cellulose, and from 14 wt % to 18 wt % of an antistatic agent such as magnesium stearate or hydrated magnesium silicate, where wt % is based on the total weight of the functional coating.

A modified release granule or granulation provided by the present disclosure can comprise, for example, a core and a modified release coating surrounding the core. The core can comprise, for example, from 85 wt % to 95 wt % of 4-((L-valyl)oxy)butanoic acid, from 1 wt % to 9 wt % such as from 3 wt % to 7 wt % of a water-soluble polymer such as hydroxypropylmethyl cellulose, and from 1 wt % to 9 wt % such as from 3 wt % to 7 wt % of an antistatic agent such as magnesium stearate or hydrated magnesium silicate, where wt % is based on the total weight of the core; and the modified release coating surrounding the core can comprise, for example, from 77 wt % to 87 wt % of a water-insoluble polymer such as ethylcellulose, from 0.1 wt % to 5 wt % of a water-soluble polymer such as hydroxypropyl cellulose, and from 11 wt % to 21 wt % such as from 14 wt % to 18 wt % of an antistatic agent such as magnesium stearate or hydrated magnesium silicate, where wt % is based on the total weight of the modified release coating.

A modified release granulation provided by the present disclosure can be configured to provide for once a night dosing, once a day dosing (QD), twice a day dosing (BID), three times a day dosing (TID), or four times a day dosing (QID). For example, a modified release granulation can release substantially 100% of the 4-((L-valyl)oxy)butanoic acid over a 24-hour duration, a 12-hour duration, an 8-hour duration, or a 4-hour duration.

A coated granulation provided by the present disclosure can have a water content, for example, less than 2 wt %, less than 1.5 wt % less than 1 wt %, less than 0.5 wt % or less than 0.25 wt %, where wt % is based on the total weight of the coated granulation.

A coated granulation provided by the present disclosure can have a water content, for example, from 0.1 wt % to 2 wt %, from 0.1 wt % to 1 wt %, or from 0.2 wt % to 0.6 wt %, where wt % is based on the total weight of the coated granulation.

A coated pharmaceutical granulation can have a bulk density, for example, greater than 0.55 g/mL, greater than 0.60 g/mL, greater than 0.65 g/mL, greater than 0.70 g/mL, or greater than 0.75 g/mL.

A coated pharmaceutical granulation can have a bulk density, for example, from 0.55 g/mL to 0.80 g/mL, from 0.60 g/mL to 75 g/mL, from 0.60 g/mL to 0.70 g/mL.

Bulk density can be determined using a bulk density cylinder.

Functional coatings provided by the present disclosure can be coated onto granulations using any suitable equipment and process. Examples of suitable coating methods include Wurster fluid bed film coating processes, compression coating processes, and phase inversion processes.

A functional coating can be applied to an uncoated granulation or to a granulation comprising a seal coating provided by the present disclosure.

Examples of coating compositions are provided in the experimental examples. A coating composition refers to the composition that is applied to an uncoated granulation or a seal-coated granulation comprising to provide a coated granulation.

A functional coating composition can comprise greater than 70 wt %, greater than 75 wt %, greater than 80 wt %, greater than 85 wt %, or greater than 90 wt % of a non-aqueous solvent such as ethanol or acetone, where wt % is based on the total weight of the functional coating solution/suspension composition used to coat the granulation.

A functional coating composition can comprise, for example, less than 20 wt % water, less than 15 wt %, less than 10 wt %, or less than 5 wt % water, where wt % is based on the functional coating solution/suspension composition used to coat the granulation.

For highly water-soluble and hygroscopic pharmaceutically active ingredients such as 4-((L-valyl)oxy)butanoic acid, it can be useful to minimize the amount of water in the functional coating composition. Reducing the level of water in the functional coating solution/suspension composition can lead to static that can render the coating process problematic.

A functional coating solution/suspension composition can comprise, for example, a solids content less than 20 wt %, less than 18 wt %, less than 16 wt %, less than 14 wt %, less than 12 wt %, less than 10 wt %, less than 8 wt %, or less than 6 wt %, where wt % is based on the functional coating solution/suspension composition.

A functional coating composition can comprise a solids content, for example, from 2 wt % to 20 wt %, from 4 wt % to 16 wt %, from 4 wt % to 12 wt %, from 6 w % to 14 wt %, or from 6 wt % to 10 wt %, where wt % is based on the functional coating composition.

Examples of coating process conditions using a Wurster column inserted into a fluid bed coating equipment are provided in the experimental examples.

A pharmaceutical composition provided by the present disclosure can comprise a combination of an immediate release granulation and a modified release granulation. A pharmaceutical composition can comprise a wt % ratio of 4-((L-valyl)oxy)butanoic acid as an immediate release granulation to 4-((L-valyl)oxy)butanoic acid as a modified release granulation, for example, from 1:1 to 1:4, from 1:1 to 1:3, from 1:1 to 1:2 or from 1:2 to 1:3.

A pharmaceutical composition provided by the present disclosure can comprise from 17 wt % to 37 wt % of an immediate release granulation, from 20 wt % to 35 wt %, from 23 wt % to 32 wt %, or from 25 wt % to 29 wt % of an immediate release composition, wherein w % is based on the total weight of the immediate release granulation and the modified release granulation. A pharmaceutical composition provided by the present disclosure can comprise from 63 wt % to 83 wt % of a modified release granulation, from 65 wt % to 81 wt %, from 68 wt % to 78 wt %, or from 71 wt % to 75 wt % of a modified release composition, wherein w % is based on the total weight of the immediate release granulation and the modified release granulation.

In a pharmaceutical composition provided by the present disclosure, from 21 wt % to 41 wt % of the 4-((L-valyl)oxy)butanoic acid can be in the immediate release component, from 24 wt % to 38 wt %, from 27 wt % to 35 wt %, or from 29 wt % to 32 wt %, wherein w % is based on the total weight of the 4-((L-valyl)oxy)butanoic acid in the pharmaceutical composition. In a pharmaceutical composition provided by the present disclosure, from 59 wt % to 79 wt % of the 4-((L-valyl)oxy)butanoic acid can be in the modified release component, from 62 wt % to 76 wt %, from 65 wt % to 73 wt %, or from 68 wt % to 62 wt %, wherein w % is based on the total weight of the 4-((L-valyl)oxy)butanoic acid in the pharmaceutical composition.

A pharmaceutical composition provided by the present disclosure can comprise a coated granulation provided by the present disclosure.

A pharmaceutical composition can comprise any suitable dosage form for oral administration.

Examples of suitable oral dosage forms include tablets, capsules, caplets, sachets, bottles, stick packs, dispersions, and suspensions.

An oral dosage form provided by the present disclosure can comprise, for example, from 0.1 grams to 20 grams of 4-((L-valyl)oxy)butanoic acid, from 0.1 grams to 15 grams, from 0.1 grams to 12 grams, from 0.1 grams to 10 grams, from 0.2 grams to 8 grams, from 0.5 grams to 5 grams, from 1 gram to 4.5 grams, or from 1.5 grams to 4 grams of 4-((L-valyl)oxy)butanoic acid. An oral dosage form can comprise, for example, greater than 0.5 grams, greater than 1 gram, greater than 2 grams, greater than 3 grams, greater than 4 grams, greater than 6 grams, or greater than 8 grams greater than 10 grams, greater than 14 grams, or greater than 18 grams of 4-((L-valyl)oxy)butanoic acid.

An oral composition provided by the present disclosure can comprise an oral suspension of coated granules having a modified release functional coating provided by the present disclosure. An oral composition can comprise a modified release granulation provided by the present disclosure and an immediate release granulation.

An oral composition can comprise a combination of an immediate release granulation and a modified release granulation provided by the present disclosure.

An oral composition provided by the present disclosure can provide a therapeutically effective amount of 4-((L-valyl)oxy)butanoic acid over a period of time.

For example, an oral composition provided by the present disclosure can provide a therapeutically effective amount of 4-((L-valyl)oxy)butanoic acid over a period of 3 hours, 6, hours 8, hours, or 10 hours.

An oral composition provided by the present disclosure can provide a therapeutically effective amount of 4-((L-valyl)oxy)butanoic acid over a period from 4 hours to 12 hours, from 4 hours to 10 hours, or from 4 hours to 8 hours.

An oral composition provided by the present disclosure can provide a therapeutically effective amount of 4-((L-valyl)oxy)butanoic acid over a duration from 1 hour to 12 hours following oral administration, from 2 hours to 10 hours, or from 4 hours to 8 hours following oral administration.

An oral composition provided by the present disclosure can be a once nightly composition. For a once nightly composition, a patient can administer a dose of 4-((L-valyl)oxy)butanoic acid before going to bed and sleep through the night such as for 6 hours or for 8 hours without having to administer a second dose during the night.

An oral composition provided by the present disclosure can provide a therapeutically effective amount of a γ-hydroxybutyric acid in the plasma of a patient.

An oral composition provided by the present disclosure can provide a therapeutically effective amount of γ-hydroxybutyric acid in the plasma of a patient for a period of 4 hours, 6, hours, 8 hours, or 10 hours following oral administration of the modified release oral composition.

An oral composition provided by the present disclosure can provide a plasma concentration of γ-hydroxybutyric acid greater than 10 μg/mL for more than 4 hours, more than 6 hours, more than 8 hours, or more than 10 hours following oral administration of the modified release oral composition.

An oral composition provided by the present disclosure can provide a plasma concentration of γ-hydroxybutyric acid greater than 15 μg/mL for more than 4 hours, more than 6 hours, more than 8 hours, or more than 10 hours following oral administration of the modified release oral composition.

An oral composition provided by the present disclosure can provide a therapeutically effective amount of $C_{max}$ to $C_{min}$ ratio of γ-hydroxybutyric acid in the plasma of a patient from less than 3 or less than 2 for a duration of 4 hours, 6 hours, 8 hours, or 10 hours following oral administration of the modified release oral composition.

An oral composition provided by the present disclosure can comprise a γ-hydroxybutyric acid derivative of Formula (2) and can comprise, for example, 0.5 g-equivalents γ-hydroxybutyric acid, 1 g-equivalents, 2 g-equivalents, 3 g-equivalents, 4 g-equivalents, 5 g-equivalents, 6 g-equivalents, 7 g-equivalents, 8 g-equivalents, 9 g-equivalents, 10 g-equivalents, 11 g-equivalents, or 12 g-equivalents γ-hydroxybutyric acid.

A pharmaceutical composition provided by the present disclosure can be included in a kit that may be used to administer the compound to a patient for therapeutic purposes. A kit can include a pharmaceutical composition comprising an immediate release component and a modified release component suitable for administration to a patient and instructions for administering the pharmaceutical composition to the patient. The kit can be used, for example, to treat a sleep disorder. A kit can comprise an immediate release component and a modified release component, a pharmaceutically acceptable vehicle for administering the immediate release component and a modified release component, and instructions for administering the pharmaceutical composition to a patient.

Oral compositions provided by the present disclosure can be provided, for example, as sachets containing a coated granulation provided the present disclosure. A sachet can be provided in different doses of 4-((L-valyl)oxy)butanoic acid such as 0.5 g, 1 g, 2 g, 3 g, 4 g, 5 g, 6 g, 7 g, 8 g, 9 g, 10 g, 11 g, 10 g, 12 g, 15 g, or 20 g of 4-((L-valyl)oxy)butanoic acid. The coated granulation can be combined, for example, with water to provide an orally ingestible dosage form.

An oral dosage form comprising crystalline 4-((L-valyl)oxy)butanoic acid can comprise an immediate release component and a modified release component.

For example, an immediate release component can comprise a solution comprising 4-((L-valyl)oxy)butanoic acid or immediate release granules comprising 4-((L-valyl)oxy)butanoic acid.

For example, a modified release component can comprise modified release granules comprising crystalline 4-((L-valyl)oxy)butanoic acid.

A combined release oral dosage form can comprise modified release granules comprising crystalline 4-((L-valyl)oxy)butanoic acid suspended in a solution comprising crystalline 4-((L-valyl)oxy)butanoic acid.

An oral dosage form can comprise granules. For example, an oral dosage form can comprise immediate release granules and modified release granules. For example, an oral dosage form can comprise a suspension containing crystalline 4-((L-valyl)oxy)butanoic acid. An oral dosage form can comprise a suspension of immediate release granules comprising crystalline 4-((L-valyl)oxy)butanoic acid and modified release granules comprising crystalline 4-((L-valyl)oxy)butanoic acid. An oral dosage form can comprise crystalline 4-((L-valyl)oxy)butanoic acid dissolved in a solution such as an aqueous solution and modified release granules comprising crystalline 4-((L-valyl)oxy)butanoic acid suspended in the solution.

A pharmaceutical composition and dosage form provided by the present disclosure can comprise any suitable excipient, salt, acid, pH-mediating, adjusting or buffering compound or agent, flavoring, solution, solvent, dispersion, glycerol, glycol, oil, antibacterial and antifungal agents, antibiotics and antihistamines, binders, disintegrating agents, lubricants, sweetening agents, or any other suitable additive or ingredient.

Examples of suitable oral formulations and oral dosage forms are disclosed in U.S. Application Publication No. 2021/0393537, U.S. Pat. No. 11,304,906, U.S. Application Publication No. 2022/0023247, U.S. Pat. Nos. 11,395,801, and 11,510,892, each of which is incorporated by reference in its entirety.

An oral formulation can comprise a combination of an immediate release granulation and a modified release granulation.

An oral formulation provided by the present disclosure can provide a therapeutically effective amount of γ-hydroxybutyric acid over a period of time in the plasma of a patient. For example, an oral formulation provided by the present disclosure can provide a therapeutically effective amount of γ-hydroxybutyric acid over a period of 3 hours, 6 hours, 8 hours, or 10 hours.

An oral formulation provided by the present disclosure can provide a therapeutically effective amount of γ-hydroxybutyric acid over a period from 4 hours to 12 hours, from 4 hours to 10 hours, or from 4 hours to 8 hours.

An oral formulation provided by the present disclosure can provide a therapeutically effective amount of γ-hydroxybutyric acid over a duration, for example, from 1 hour to 12 hours following oral administration, from 2 hours to 10 hours or from 4 hours to 8 hours following oral administration.

An oral formulation provided by the present disclosure can be a once nightly formulation. For a once nightly formulation, a patient can administer a dose of crystalline 4-((L-valyl)oxy)butanoic acid and/or γ-hydroxybutyric acid as a prodrug provided by the present disclosure before going to bed and sleep through the night such as for 6 hours or for 8 hours without having to administer a second dose during the night.

An oral formulation provided by the present disclosure can provide a therapeutically effective amount of γ-hydroxybutyric acid in the plasma of a patient. An oral formulation provided by the present disclosure can provide a therapeutically effective amount of γ-hydroxybutyric acid in the plasma of a patient for a period of 4 hours, 6 hours, 8 hours, or 10 hours following oral administration of the modified release oral formulation.

An oral formulation provided by the present disclosure can provide a plasma concentration of γ-hydroxybutyric acid, for example, greater than 10 μg/mL for more than 4 hours, for more than 6 hours, for more than 8 hours, or for more than 10 hours following oral administration of the oral formulation.

An oral formulation provided by the present disclosure can provide a plasma concentration of γ-hydroxybutyric acid, for example, greater than 15 μg/mL for more than 4 hours, for more than 6 hours, for more than 8 hours, or for more than 10 hours following oral administration of the oral formulation.

An oral formulation provided by the present disclosure can provide a therapeutically effective amount of $C_{max}$ to $C_{min}$ ratio of γ-hydroxybutyric acid in the plasma of a patient, for example, from less than 3 or less than 2 for a duration of 4 hours, 6 hours, 8 hours, or 10 hours following oral administration of the modified release oral formulation.

An oral formulation provided by the present disclosure can comprise a crystalline 4-((L-valyl)oxy)butanoic acid and can comprise, for example, 0.5 g-equivalents of γ-hydroxybutyric acid, 1 g-equivalents, 2 g-equivalents, 3 g-equivalents, 4 g-equivalents, 5 g-equivalents, 6 g-equivalents, 7 g-equivalents, 8 g-equivalents, 9 g-equivalents, 10 g-equivalents, 11 g-equivalents, or 12 g-equivalents of γ-hydroxybutyric acid. An oral formulation provided by the present disclosure can comprise a crystalline 4-((L-valyl)oxy)butanoic acid and can comprise, for example, from 0.5 g-equivalents to 12 g-equivalents of γ-hydroxybutyric acid, from 1 g-equivalents to 12 g-equivalents, from 2 g-equivalents to 12 g-equivalents, from 3 g-equivalents to 11 g-equivalents, from 4 g-equivalents to 10 g-equivalents, or from 5 g-equivalents to 9 g-equivalents of γ-hydroxybutyric acid. An oral formulation provided by the present disclosure can comprise, for example, greater than 0.5 g-equivalents of γ-hydroxybutyric acid, greater than 1 g-equivalents, greater than 3 g-equivalents, greater than 5 g-equivalents, greater than 7 g-equivalents, greater than 9 g-equivalents, or greater than 11 g-equivalents of γ-hydroxybutyric acid.

An oral formulation provided by the present disclosure can comprise a suspension such as an aqueous suspension of immediate release and controlled release granules comprising crystalline 4-((L-valyl)oxy)butanoic acid. The core of the granules can comprise greater than 90 wt % such as greater than 94 wt %, or greater than 96 wt % of crystalline 4-((L-valyl)oxy)butanoic acid, where wt % is based on the total weight of the granule core.

An oral formulation provided by the present disclosure can be provided, for example, as a sachet or package containing an immediate release component such as immediate release granules comprising crystalline 4-((L-valyl)oxy)butanoic acid and a modified release component such as modified release granules comprising crystalline 4-((L-valyl)oxy)butanoic acid. A sachet or package can be provided in different dose equivalents of γ-hydroxybutyric acid such as 0.5 g, 1 g, 2 g, 3 g, 4 g, 5 g, 6 g, 7 g, 8 g, 9 g, 10 g, 11 g, 10 g, 12 g, 15 g, or 20 g-equivalents of γ-hydroxybutyric acid.

An oral dosage form such as a coated granulation comprising immediate release granules and modified release granules can be combined, for example, with water to provide an orally ingestible dosage form.

Crystalline 4-((L-valyl)oxy)butanoic acid or a pharmaceutical composition thereof can be included in a kit that may be used to administer the compound to a patient for therapeutic purposes. A kit can include a pharmaceutical composition comprising crystalline 4-((L-valyl)oxy)butanoic acid suitable for administration to a patient and instructions for administering the pharmaceutical composition to the patient. The kit can be used, for example, to treat a sleep disorder. A kit can comprise crystalline 4-((L-valyl)oxy)butanoic acid, a pharmaceutically acceptable vehicle for administering crystalline 4-((L-valyl)oxy)butanoic acid, and instructions for administering crystalline 4-((L-valyl)oxy)butanoic acid to a patient.

A pharmaceutical composition can be included in a container, pack, or dispenser together with instructions for administration.

Instructions supplied with a kit may be printed and/or supplied, for example, as an electronic-readable medium, a video cassette, an audiotape, a flash memory device, or may be accessible on an internet web site or distributed to a patient and/or health care provider as an electronic communication.

Crystalline 4-((L-valyl)oxy)butanoic acid can be metabolized in the systemic circulation of a patient to provide γ-hydroxybutyric acid.

Methods provided by the present disclosure include providing a therapeutically effective amount of γ-hydroxybutyric acid in the systemic circulation of a patient for treating a disease or disorder in a patient or a symptom of a disease or disorder in a patient comprising administering to a patient crystalline 4-((L-valyl)oxy)butanoic acid, or a pharmaceutical composition thereof.

A suitable dose of crystalline 4-((L-valyl)oxy)butanoic acid can provide, for example, a dose of from 1 gram-equivalents to 12 gram-equivalents of γ-hydroxybutyric acid, such as a dose from 1 gram-equivalents to 10 gram-equivalents, from 2 gram-equivalents to 9 gram-equivalents, from 3 gram-equivalents to 8 gram-equivalents, or from 4 gram-equivalents to 7 gram-equivalents of γ-hydroxybutyric acid.

It will be understood, however, that the specific dose level and frequency of dosage for any particular patient may be varied and will depend upon a variety of factors including: the metabolic stability and length of action, the age, body weight, general health, gender, diet, mode and time of administration, rate of excretion, drug combination, the severity of the particular condition, and the host undergoing therapy.

When initiating treatment with crystalline 4-((L-valyl)oxy)butanoic acid, titration up to an adequate plasma concentration can facilitate obtaining positive results and avoid adverse effects. For example, a dose can be 4.5 g-equivalents of γ-hydroxybutyric acid divided into 2 equal doses of 2.25 g, the first taken at bedtime and the second taken 2.5 hours to 4 hours later. The starting dose can be decreased to 3.0 g/day or increased to as high as 9.0 g/day in increments of 1.5 g/day (0.75 g per dose). A dose can provide an effective eight hours of sleep but, at the end of eight hours, little of the γ-hydroxybutyric acid will remain in the plasma of a patient.

A pharmaceutical composition provided by the present disclosure can be configured to provide for once a night dosing, once a day dosing (QD), twice a day dosing (BID), three times a day dosing (TID), or four times a day dosing (QID). For example, a pharmaceutical composition comprising a modified release granulation can release substantially 100% of crystalline 4-((L-valyl)oxy)butanoic acid over a 24-hour duration, a 12-hour duration, an 8-hour duration, or a 4-hour duration.

Crystalline 4-((L-valyl)oxy)butanoic acid is a prodrug of γ-hydroxybutyric acid.

Crystalline 4-((L-valyl)oxy)butanoic acid can be used to treat any disease or disorder that is known to be treated by γ-hydroxybutyric acid or is determined to be treated by γ-hydroxybutyric acid.

For example, crystalline 4-((L-valyl)oxy)butanoic acid can be used to treat narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's disease, fatigue associated with multiple sclerosis, and fibromyalgia.

Crystalline 4-((L-valyl)oxy)butanoic acid can be used to treat REM sleep behavior disorder, spasmodic dystonia, schizophrenia, insomnia, insomnia associated with schizophrenia, idiopathic hypersomnia, chronic fatigue syndrome, cluster headache, symptoms of Alzheimer's disease, essential tremor, post-traumatic stress syndrome, insomnia associated with post-traumatic stress syndrome, and anxiety.

Crystalline 4-((L-valyl)oxy)butanoic acid can be used to treat excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, or fibromyalgia.

Crystalline 4-((L-valyl)oxy)butanoic acid and pharmaceutical compositions thereof can be used to treat a sleep disorders such as apnea, a sleep time disturbance, narcolepsy, cataplexy, sleep paralysis, hypnagogic hallucination, sleep arousal, insomnia, and nocturnal myoclonus.

Crystalline 4-((L-valyl)oxy)butanoic acid or a pharmaceutical composition thereof can be used to treat a disease selected from narcolepsy, cataplexy, cataplexy with narcolepsy, excessive daytime sleepiness, a sleep disorder associated with Parkinson's disease, symptoms of Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep ignition and maintenance disorders, chronic fatigue syndrome, essential tremor, hemiplegia in patients with alternating hemiplegia of childhood, sedative abuse, and binge eating disorder.

For certain methods of treatment the effectiveness of the treatment can be measured by one or more of the following criteria: increase in the mean sleep latency such as determined the Maintenance of Wakefulness Test (MWT); improvement in the Clinical Global Impression (CGI) rating of sleepiness; decrease in the number of cataplexy attacks (NCA) such as determined from the cataplexy frequency item in the Sleep and Symptoms Daily Diary; decrease in disturbed nocturnal sleep (DNS), the disturbed nocturnal events or the adverse respiratory events such as determined by polysomnographic (PSG) measures of sleep fragmentation; decrease in excessive daytime sleepiness (EDS) such as measured by patient report via the Epworth Sleepiness Scale (ESS); decrease in daytime sleepiness as measured by the Maintenance of Wakefulness Test based on EEG measures of wakefulness; decrease PSG transitions from N/2 to N/3 and REM sleep to wake and N1 sleep such a determined as described in the AASM Manual for the Scoring of Sleep and Associated Events; decrease in the number of arousals or wakenings such as determined from a PSG as defined by the American Academy of Sleep Medicine; improvement in sleep quality such as determined using (i) the Sleep and Symptom Daily Diary, (ii) Visual Analog Scale (VAS) for sleep quality and sleep diary, and/or (iii) VAS for the refreshing nature of sleep; and decrease in the Hypnagogic Hallucinations (HH) or sleep paralysis (SP) symptoms in NT1 narcolepsy patients such as measured by the Sleep and Symptom Daily Diary.

Type 1 Narcolepsy (NT1) refers to narcolepsy characterized by excessive daytime sleepiness ("EDS") and cataplexy. Type 2 Narcolepsy (NT2) refers to narcolepsy characterized by excessive daytime sleepiness without cataplexy. A diagnosis of narcolepsy (with or without cataplexy) can be confirmed by one or a combination of (i) an overnight polysomnogram (PSG) and a Multiple Sleep Latency Test (MSLT) performed within the last 2 years, (ii) a full documentary evidence confirming diagnosis from the PSG and MSLT from a sleep laboratory must be made available, (iii) current symptoms of narcolepsy including: current complaint of EDS for the last 3 months (Epworth Sleepiness Scale (ESS) greater than 10), (iv) mean Maintenance of Wakefulness Test (MWT) less than 8 minutes, (v) mean number of cataplexy events of 8 per week on baseline Sleep/Cataplexy Diary, and/or (vi) presence of cataplexy for the last 3 months and 28 events per week during screening period.

Aspects of the Invention

The invention is further defined by the following aspects.

Aspect 1. A compound, crystalline 4-((L-valyl)oxy)butanoic acid:

(1)

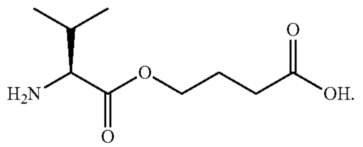

Aspect 2. The compound of aspect 1, wherein the compound is characterized by an XRPD pattern comprising characteristic diffraction peaks at least at 8.28°±0.20°, 16.75°±0.20°, and 25.33±0.20° expressed as °2θ angles determined using Cu-Kα radiation.

Aspect 3. The compound of aspect 1, wherein the compound is characterized by an XRPD pattern comprising characteristic diffraction peaks at least at 8.28°±0.20°, 16.75°±0.20°, 17.64°±0.20°, 18.31°±0.20°, 19.42°±0.20°, 20.79°±0.20°, 25.33±0.20°, and 26.08°±0.20° expressed as °2θ angles determined using Cu-Kα radiation.

Aspect 4. The compound of aspect 1, wherein the compound is characterized by an XRPD pattern comprising characteristic diffraction peaks at least at 8.28°±0.20°, 9.58°±0.20°, 13.75°±0.20°, 16.75°±0.20°, 17.64°±0.20°, 18.31°±0.20°, 19.42°±0.20°, 20.79°±0.20°, 24.98°±0.20°, 25.33±0.2°, and 26.08°±0.20° expressed as °2θ angles determined using Cu-Kα radiation.

Aspect 5. The compound of aspect 1, wherein the compound is characterized by an XRPD pattern comprising characteristic diffraction peaks at least at 8.28°±0.20°, 9.58°±0.20°, 11.63°±0.20°, 13.75°±0.20°, 16.75°±0.20°, 17.64°±0.20°, 19.93°±0.20°, 18.31°±0.20°, 19.42°±0.20°, 20.79°±0.20°, 22.22°±0.20°, 23.58°±0.20°, 24.98°±0.20°, 25.33±0.20°, and 26.08°±0.20° expressed as °2θ angles determined using Cu-Kα radiation.

Aspect 6. The compound of aspect 1, wherein the compound is characterized by an XRPD pattern comprising characteristic diffraction peaks at least at 8.28°±0.10°, 16.75°±0.10°, and 25.33±0.10° expressed as °2θ angles determined using Cu-Kα radiation.

Aspect 7. The compound of aspect 1, wherein the compound is characterized by an XRPD pattern comprising characteristic diffraction peaks at least at 8.28°±0.10°, 16.75°±0.10°, 17.64°±0.10°, 18.31°±0.10°, 19.42°±0.10°, 20.79°±0.10°, 25.33±0.10°, and 26.08°±0.10° expressed as °2θ angles determined using Cu-Kα radiation.

Aspect 8. The compound of aspect 1, wherein the compound is characterized by an XRPD pattern comprising characteristic diffraction peaks at least at 8.28°±0.20°, 9.58°±0.20°, 13.75°±0.10°, 16.75°±0.10°, 17.64°±0.10°, 18.31°±0.10°, 19.42°±0.10°, 20.79°±0.10°, 24.98°±0.10°, 25.33±0.10°, and 26.08°±0.10° expressed as °2θ angles determined using Cu-Kα radiation.

Aspect 9. The compound of aspect 1, wherein the compound is characterized by an XRPD pattern comprising characteristic diffraction peaks at least at 8.28°±0.10°, 9.58°±0.10°, 11.63°±0.10°, 13.75°±0.10°, 16.75°±0.10°, 17.64°±0.10°, 19.93°±0.10°, 18.31°±0.10°, 19.42°±0.10°, 20.79°±0.10°, 22.22°±0.10°, 23.58°±0.10°, 24.98°±0.10°, 25.33±0.10°, and 26.08°±0.10° expressed as °2θ angles determined using Cu-Kα radiation.

Aspect 10. The compound of aspect 1, wherein the compound is characterized by an XRPD pattern as shown in FIG. 1.

Aspect 11. The compound of any one of aspects 1 to 10, wherein the compound has a melting onset temperature from 135° C. to 141° C., wherein the melting onset temperature is determined by differential scanning calorimetry.

Aspect 12. The compound of any one of aspects 1 to 10, wherein the compound has a melting onset temperature is 137.7° C.±1.0° C., wherein the melting onset temperature is determined by differential scanning calorimetry.

Aspect 13. The compound of any one of aspects 1 to 12, wherein the compound has a melting enthalpy from 197 J/g to 207 J/g, wherein the melting enthalpy is determined by differential scanning calorimetry.

Aspect 14. The compound of any one of aspects 1 to 12, wherein the compound has a melting enthalpy is 202.2 J/g+1.0 J/g, wherein the melting enthalpy is determined by differential scanning calorimetry.

Aspect 15. The compound of any one of aspects 1 to 14, wherein the compound has a melting peak temperature from 138.0° C. to 142.0° C., wherein the melting peak temperature is determined by differential scanning calorimetry.

Aspect 16. The compound of any one of aspects 1 to 14, wherein the compound has a melting peak temperature is 139.9° C.±2.0° C., wherein the melting peak temperature is determined by differential scanning calorimetry.

Aspect 17. The compound of any one of aspects 1 to 16, wherein the compound exhibits a differential scanning calorimetry curve as shown in FIG. 2.

Aspect 18. The compound of any one of aspects 1 to 17, wherein the compound has a weight loss from 0.16 wt % to 0.36 wt % over a temperature range from 20° C. to 70° C., wherein the weight loss is determined by thermogravimetric analysis at a scan rate of 2° C./min.

Aspect 19. The compound of any one of aspects 1 to 17, wherein the compound has a weight loss of 0.26 wt %±0.20 wt % over a temperature range from 20° C. to 70° C., wherein the weight loss is determined by thermogravimetric analysis at a scan rate of 2° C./min.

Aspect 20. The compound of any one of aspects 1 to 19, wherein the compound exhibits a differential thermal calorimetry curve as shown in FIG. 2.

Aspect 21. The compound of any one of aspects 1 to 20, wherein the compound has a water content from 5.8 mol % to 6.6 mol %, wherein mol % is based on the total moles of 4-((L-valyl)oxy)butanoic acid and water in the crystalline 4-((L-valyl)oxy)butanoic acid, and the water content is determined using Karl Fischer analysis.

Aspect 22. The compound of any one of aspects 1 to 21, wherein the compound has a water content of less than 5 wt %, wherein wt % is based on the total weight of 4-((L-valyl)oxy)butanoic acid and water in the crystalline 4-((L-valyl)oxy)butanoic acid, and the water content is determined using Karl Fischer analysis.

Aspect 23. The compound of any one of aspects 1 to 22, wherein the compound absorbs less than 2 wt % water at conditions of 25° C./60% RH for 36 months.

Aspect 24. The compound of any one of aspects 1 to 23, wherein the compound has an impurity content of less than 1 wt % at conditions of 25° C./60% RH for 36 months.

Aspect 25. The compound of any one of aspects 1 to 24, wherein the compound has a water content of less than 5 wt % and an impurity content of less than 5 wt % after storage at 25° C./60% RH for 6 months, wherein wt % is based on the total weight of the compound, water, and impurity; the water content is determined using Karl Fischer analysis, and the impurity content is determined using high pressure liquid chromatography.

Aspect 26. The compound of any one of aspects 1 to 25, wherein the un-milled compound has a particle size distribution characterized by a D10 from 7 μm to 17 μm, a D50 of 29 μm to 39 μm, and a D90 of 67 μm to 75 μm, wherein particle size is determined by sieve analysis or by laser diffraction.

Aspect 27. The compound of any one of aspects 1 to 26, wherein the un-milled compound has a particle size distribution characterized by a D[4,3] from 35 μm to 41 μm, wherein particle size is determined by sieve analysis or by laser diffraction.

Aspect 28. The compound of any one of aspects 1 to 27, wherein the un-milled compound has a uniformity from 0.45 to 0.65, wherein uniformity is determined using laser diffraction.

Aspect 29. The compound of any one of aspects 1 to 28, wherein the un-milled compound has a surface area of 270 $m^2/kg$ to 310 $m^2/kg$, wherein surface area is determined using laser diffraction.

Aspect 30. The compound of any one of aspects 1 to 29, wherein the un-milled compound has a bulk density from 0.15 g/mL to 0.25 g/mL, wherein bulk density is determined according to USP 616, Method 1.

Aspect 31. The compound of any one of aspects 1 to 30, wherein the un-milled compound has a Hausner ratio from 1.65 to 1.95, wherein the Hausner ratio is determined according to USP 1174.

Aspect 32. The compound of any one of aspects 1 to 31, wherein the milled compound has a particle size distribution characterized by a D10 from 1 μm to 5 μm, a D50 of 4 μm to 8 μm, and a D90 of 10 μm to 14 μm, wherein particle size is determined by sieve analysis or by laser diffraction.

Aspect 33. The compound of any one of aspects 1 to 32, wherein the milled compound has a particle size distribution characterized by a D[4,3] from 12 μm to 22 μm, wherein particle size is determined by sieve analysis or by laser diffraction.

Aspect 34. The compound of any one of aspects 1 to 33, wherein the milled compound has a uniformity from 0.2 to 0.6, wherein uniformity is determined by laser diffraction.

Aspect 35. The compound of any one of aspects 1 to 34, wherein the milled compound has a surface area of 430 $m^2/kg$ to 630 $m^2/kg$, wherein surface area is determined by laser diffraction.

Aspect 36. The compound of any one of aspects 1 to 35, wherein the milled compound has a bulk density from 0.10 g/mL to 0.14 g/mL, wherein bulk density is determined according to USP 616, Method 1.

Aspect 37. The compound of any one of aspects 1 to 36, wherein the milled compound has a Hausner ratio from 1.6 to 1.8, wherein the Hausner ratio is determined according to USP 1174.

Aspect 38. A granulation comprising a plurality of granules comprising the compound of any one of aspects 1 to 37.

Aspect 39. The granulation of aspect 38, wherein the granules have an average particle size from 100 μm to 550 μm.

Aspect 40. The granulation of any one of aspects 38 to 39, wherein the granules comprise greater than 80 wt % of the compound, wherein wt % is based on the total weight of the granules.

Aspect 41. The granulation of any one of aspects 38 to 40, wherein the granules comprise a core comprising greater than 80 wt % of the compound, and a modified release coating surrounding the core.

Aspect 42. The granulation of any one of aspects 38 to 41, wherein the granulation comprises immediate release granules and modified release granules.

Aspect 43. A pharmaceutical composition comprising the compound of any one of aspects 1 to 37 or the granulation of any one of aspects 38 to 42.

Aspect 44. The pharmaceutical composition of aspect 43, wherein the pharmaceutical composition comprises a therapeutically effective amount of the compound for treating a disease in a patient, wherein the disease is selected from narcolepsy, cataplexy, cataplexy with narcolepsy, excessive daytime sleepiness, a sleep disorder associated with Parkinson's disease, Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep ignition and maintenance disorders, chronic fatigue syndrome.

Aspect 45. The pharmaceutical composition of any one of aspects 43 to 44, wherein the pharmaceutical composition comprises an oral formulation.

Aspect 46. The pharmaceutical composition of any one of aspects 43 to 45, wherein the pharmaceutical composition comprises from 1 gram-equivalents to 10 gram-equivalents of γ-hydroxybutyric acid.

Aspect 47. The pharmaceutical composition of any one of aspects 43 to 46, wherein the pharmaceutical composition comprises from 1 grams to 20 grams of crystalline 4-((L-valyl)oxy)butanoic acid.

Aspect 48. The pharmaceutical composition of any one of aspects 43 to 47, wherein the pharmaceutical composition comprises an immediate release component and a modified release component.

Aspect 49. The pharmaceutical composition of aspect 48, wherein the immediate release component comprises a solution comprising 4-((L-valyl)oxy)butanoic acid.

Aspect 50. The pharmaceutical composition of aspect 48, wherein the immediate release component comprises immediate release granules comprising crystalline 4-((L-valyl)oxy)butanoic acid.

Aspect 51. The pharmaceutical composition of any one of aspects 48 to 50, wherein the modified release component comprises modified release granules comprising crystalline 4-((L-valyl)oxy)butanoic acid.

Aspect 52. An oral dosage form comprising the compound of any one of aspects 1 to 38, the granulation of any one of aspects 39 to 42, or the pharmaceutical composition of any one of aspects 43 to 51.

Aspect 53. The oral dosage form of aspect 52, wherein the oral dosage form comprises from 1 gram-equivalents to 10 gram-equivalents of γ-hydroxybutyric acid.

Aspect 54. The oral dosage form of any one of aspects 52 to 53, wherein the oral dosage form comprises from 1 grams to 20 grams of crystalline 4-((L-valyl)oxy)butanoic acid.

Aspect 55. The oral dosage form of any one of aspects 52 to 54, wherein the oral dosage form comprises an immediate release component and a modified release component.

Aspect 56. The oral dosage form of aspect 55, wherein the immediate release component comprises a solution comprising 4-((L-valyl)oxy)butanoic acid.

Aspect 57. The oral dosage form of aspect 55, wherein the immediate release component comprises immediate release granules comprising crystalline 4-((L-valyl)oxy)butanoic acid.

Aspect 58. The oral dosage form of any one of aspects 55 to 57, wherein the modified release component comprises modified release granules comprising crystalline 4-((L-valyl)oxy)butanoic acid.

Aspect 59. The oral dosage form of any one of aspects 55 to 56, wherein the oral dosage form comprises modified release granules comprising crystalline 4-((L-valyl)oxy)butanoic acid suspended in a solution comprising 4-((L-valyl)oxy)butanoic acid.

Aspect 60. A kit comprising the compound of any one of aspects 1 to 38, the granulation of any one of aspects 39 to 42, or the pharmaceutical composition of any one of aspects 43 to 51.

Aspect 61. The kit of aspect 60, wherein the kit comprises an immediate release component comprising crystalline 4-((L-valyl)oxy)butanoic acid and a modified release component comprising crystalline 4-((L-valyl)oxy)butanoic acid.

Aspect 62. The kit of any one of aspect 61, wherein the immediate release component comprises immediate release granules comprising crystalline 4-((L-valyl)oxy)butanoic acid and the modified release component comprises modified release granules comprising crystalline 4-((L-valyl)oxy) butanoic acid.

Aspect 63. The kit of any one of aspects 60 to 62, wherein the pharmaceutical composition or oral dosage form is contained within a sachet.

Aspect 64. A method of treating a disease in a patient comprising administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of aspects 52 to 59, wherein the disease is capable of being treated with γ-hydroxybutyric acid.

Aspect 65. A method of treating a disease in a patient comprising administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of aspects 52 to 59, wherein the disease is selected from narcolepsy, cataplexy, cataplexy with narcolepsy, excessive daytime sleepiness, a sleep disorder associated with Parkinson's disease, Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep ignition and maintenance disorders, chronic fatigue syndrome, essential tremor, hemiplegia in patients with alternating hemiplegia of childhood, sedative abuse, and binge eating disorder.

Aspect 66. A method of treating fatigue or excessive daytime sleepiness associated with narcolepsy comprising orally administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of aspects 52 to 59.

Aspect 67. A method of treating narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia comprising orally administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of aspects 52 to 59.

Aspect 68. The method of aspect 67, wherein the disease is cataplexy associated with narcolepsy.

Aspect 69. The method of aspect 67, wherein the disease is excessive daytime sleepiness associated with narcolepsy.

Aspect 70. The method of aspect 67, wherein the disease is excessive daytime sleepiness in a patient with Parkinson's disease.

Aspect 71. The method of aspect 67, wherein the disease is chronic fatigue in a patient with Parkinson's disease.

Aspect 72. A method of treating a symptom associated with narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia comprising orally administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of 52 to 59

Aspect 73. A method of treating an REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety comprising orally administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of 52 to 59.

Aspect 74. A method of treating a symptom associated with REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety comprising orally administering to a patient in need of such treatment a therapeutically effective amount of the compound of any one of aspects 1 to 37, the granulation of any one of aspects 39 to 42, the pharmaceutical composition of any one of aspects 43 to 51, or the oral dosage form of any one of 52 to 59.

Aspect 75. The method of any one of aspects 63 to 74, wherein administering comprises orally administering.

Aspect 76. The method of any one of aspects 63 to 75, wherein administering comprises administering QD.

Aspect 77. The method of any one of aspects 63 to 75, wherein administering comprises administering BID.

Aspect 78. A method of preparing the compound of any one of aspects 1 to 37, comprising:

(i) dissolving 4-((L-valyl)oxy)butanoic acid in a first solvent to obtain a solution; and (ii) crystallizing the solution to obtain crystalline 4-((L-valyl)oxy)butanoic acid.

Aspect 79. The method of aspect 78, wherein the first solvent is selected from methanol, ethanol, isopropanol, tetrahydrofuran, ethyl acetate, acetone, isobutanol, isopropyl acetate, acetonitrile, 2-butanone, toluene, water, tert-butyl methyl ether, n-propanol, isopentanol, butyl acetate, ethyl formate, methyl acetate, isobutyl acetate, n-heptane, dichloromethane, 1,4-dioxane, cyclohexane, xylene, 4-methyl-2-pentanone, ethyl ether, or a combination of any of the foregoing.

Aspect 80. The method of any one of aspects 78 to 79, wherein dissolving comprises dissolving in the first solvent at a temperature from 60° C. to 90° C.

Aspect 81. The method of any one of aspects 78 to 80, wherein the method comprises after dissolving to form a solution adding a second solvent to the solution.

Aspect 82. The method of aspect 81, wherein the second solvent is selected from acetonitrile, tetrahydrofuran, isopropanol, acetone, ethyl acetate, tert-butyl methyl ether, 1,4-dioxane, or a combination of any of the foregoing.

Aspect 83. The method of any one of aspects 78 to 82, wherein crystallizing comprises heating the solution to a temperature from 60° C. to 90° C. for from 0.5 hours to 2 hours.

Aspect 84. The method of any one of aspects 78 to 83, wherein the method comprises, after crystallizing, recrystallizing the crystalline 4-((L-valyl)oxy)butanoic acid.

EXAMPLES

The following examples describe in detail methods of preparing crystalline 4-((L-valyl)oxy)butanoic acid, properties of crystalline 4-((L-valyl)oxy)butanoic acid, and methods of using crystalline 4-((L-valyl)oxy)butanoic acid provided by the present disclosure. It will be apparent to those skilled in the art that many modifications, both to materials and methods, may be practiced without departing from the scope of the invention.

Example 1

Synthesis of (S)-4-(2-Amino-3-methylbutanoyloxy)butanoic Acid

Step 1: Preparation of (S)-4-hydroxybutyl 2-(tert-butoxycarbonylamino)-3-methylbutanoate (1a)

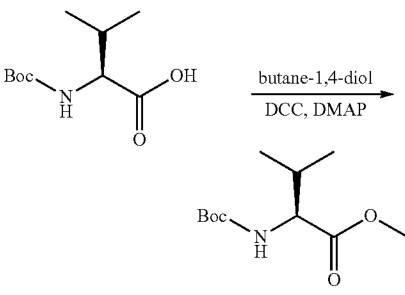

1a (S)-2-(tert-Butoxycarbonylamino)-3-methylbutanoic acid (1 g, 4.61 mmol), N,N'-dicyclohexylcarbodiimide (DCC) (1,044 mg, 5.07 mmol) and 4-dimethylaminopyridine (DMAP) (10 mg) were added to a stirred solution of butane-1,4-diol (829 mg, 9.21 mmol) in dichloromethane (DCM) (20 mL). The reaction was stirred at 25° C. for 16 h. The reaction mixture was then diluted with saturated aqueous $NH_4Cl$ (10 mL) and stirred for 5 min. The aqueous phase was separated and extracted with DCM (10 mL). The combined organic phase was washed with saturated brine (15 mL), dried over anhydrous $Na_2SO_4$, and evaporated. The residue was purified using a silica gel flash column with hexane/ethyl acetate (Hex/EA)=5:1 to yield compound (1a) (700 mg, 53%) as a colorless oil. $^1$H NMR was performed at 400 MHz with $CDCl_3$ as solvent: 6=5.07 (d, J=8.8 Hz, 1H), 4.16-4.11 (m, 3H), 3.62 (t, J=6.2 Hz, 2H), 2.32 (br. s., 1H), 2.12-2.04 (m, 1H), 1.75-1.68 (m, 2H), 1.62-1.56 (m, 2H), 1.40 (s, 9H), 0.92 (d, J=7.2 Hz, 3H), 0.85 (d, J=7.2 Hz, 3H).

Step 2: Preparation of (S)-4-(2-(tert-butoxycarbonylamino)-3-methylbutanoyloxy)butanoic acid (1b)

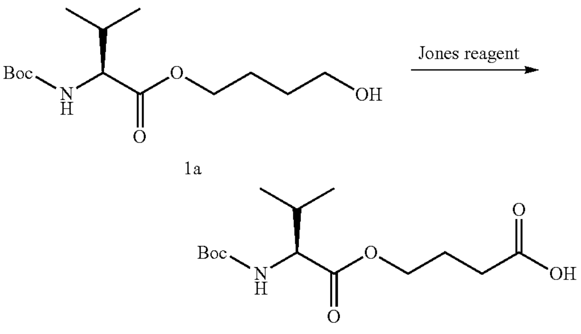

1a

1b

Jones reagent was added in portions to a stirred mixture of (S)-4-hydroxybutyl 2-(tert-butoxycarbonylamino)-3-methylbutanoate (1a) (500 mg, 1.73 mmol) and Celite® (diatomaceous earth, 2 g) in acetone (10 mL) at 0° C. The reaction proceeded at 0° C. for over 1 h and the reaction progress was monitored using thin layer chromatography (TLC). After completion, the reaction was quenched with drops of isopropanol, diluted with ethyl acetate (EA) (10 mL) and then filtered. The filter cake was washed with EA (5 mL) and the combined filtrate was washed with saturated brine (2 mL×2), dried over anhydrous $Na_2SO_4$, and concentrated. The residue was purified using a silica gel flash column with Hex/EA=10:1-5:1 to yield compound (1b) (170 mg, 32%) as a white solid. $^1$H NMR was performed at 400 MHz with $CDCl_3$ as solvent: 6=5.03 (d, J=9.2 Hz, 1H), 4.30-4.24 (m, 1H), 4.22-4.13 (m, 2H), 2.46 (t, J=7.4 Hz, 2H), 2.16-2.08 (m, 1H), 2.06-1.96 (m, 2H), 1.45 (s, 9H), 0.96 (d, J=6.8 Hz, 3H), 0.89 (d, J=6.4 Hz, 3H).

Step 3: Preparation of (S)-4-(2-amino-3-methylbutanoyloxy)butanoic acid

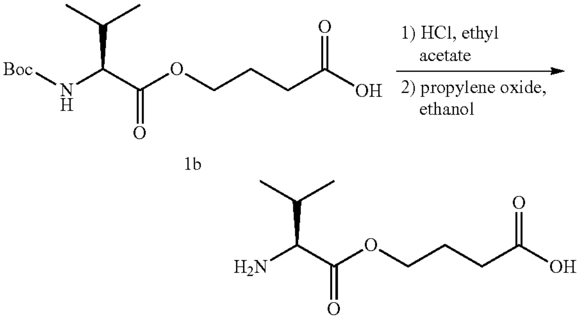

1b

1

A solution of (S)-4-(2-(tert-butoxycarbonylamino)-3-methylbutanoyloxy)butanoic acid (1b) (104 mg, 0.34 mmol) in HCl/EA (~2 M, 1.5 mL) was stirred at 25° C. for 24 h. The reaction mixture was then filter and the precipitate collected, washed with $Et_2O$ (0.5 mL), and dried in vacuo to yield the title compound (50 mg, 71%) as a white solid in HCl salt form. $^1$H NMR was performed at 400 MHz with $CD_3OD$ as solvent: δ=4.33-4.26 (m, 2H), 3.92 (d, J=4.8 Hz, 1H), 2.42 (t, J=7.2 Hz, 2H), 2.34-2.25 (m, 1H), 2.05-1.94 (m, 2H), 1.06 (d, J=6.8 Hz, 6H).

A suspension of the HCl salt (800 mg, 3.3 mmol) in ethanol (4 mL) was stirred at 80° C. for 30 min to provide a clear solution. The solution was gradually cooled to 25° C., and propylene oxide (580 mg, 10 mmol) was added dropwise. The reaction was stirred at 25° C. for 16 h and then the suspension was filtered. The white solid was collected, washed with cold ethanol, and dried in vacuo to afford compound (510 mg, 75%) as the free base. $^1H$ NMR was performed at 400 MHz with $d_6$-DMSO as solvent: δ=4.10-3.99 (m, 2H), 3.11 (d, J=5.2 Hz, 1H), 2.29 (t, J=7.4 Hz, 2H), 1.90-1.74 (m, 3H), 0.87 (d, J=6.8 Hz, 3H), 0.82 (d, J=6.4 Hz, 3H).

Example 2

Alternative Synthesis of (S)-4-(2-Amino-3-methylbutanoyloxy)butanoic Acid

Step 1: Preparation of benzyl 4-hydroxybutanoate (2a)

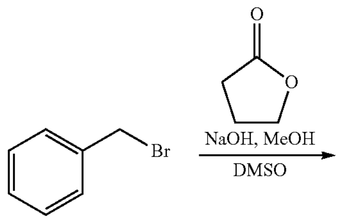

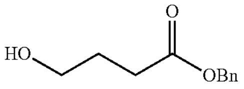

2a

Sodium hydroxide (1.0 equivalent) was dissolved in methanol (5 volumes) with stirring while maintaining the temperature below 40° C. The reaction mixture was cooled to room temperature and butyrolactone (1.0 equivalent) was added while maintaining the temperature below 30° C., and the reaction mixture was stirred for 5 to 6 hours. The reaction mixture was concentrated in vacuo while co-evaporating with tert-butyl methyl ether. The mixture was redissolved in dimethyl sulfoxide (DMSO) and benzyl bromide (0.95 equivalents) was added dropwise. The reaction mixture was stirred for 3 hours at room temperature, cooled to 15° C., and quenched with purified water. The aqueous phase was washed with tert-butyl methyl ether. The collected organics were washed with water and concentrated in vacuo while co-evaporating with dichloromethane to provide benzyl 4-hydroxybutanoate (2a) in 69.5% yield.

Step 2: Preparation of 4-(benzyloxy)-4-oxobutyl ((benzyloxy)carbonyl)-L-valinate (2b)

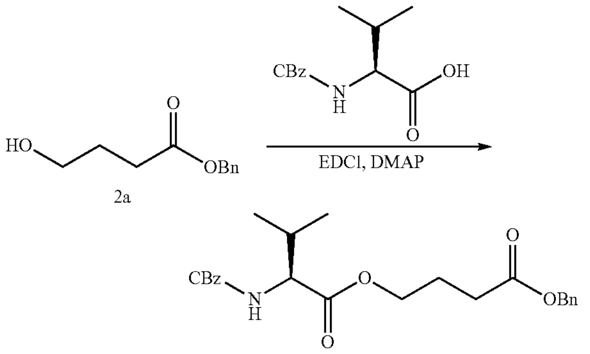

2a

2b

Benzyl 4-hydroxybutanoate (2a) (0.95 equivalents) was dissolved in dichloromethane (2.5 volumes). CBz-L-valine (1.00 equivalent) and 4-dimethylaminopyridine (DMAP) (0.20 equivalents) were added, followed by 1-ethyl-3-(3-dimethylaminopropyl) carbodiimide (EDCI) (1.20 equivalents) while maintaining the reaction mixture at 15° C. The reaction mixture was stirred for 20 hours at room temperature. 5% HCl (5 volumes) was added, and the reaction mixture was stirred for 15 minutes at room temperature. The biphasic solution was allowed to separate, and the aqueous layer was removed. The organic layer was washed with 5% sodium bicarbonate solution and purified water, concentrated in vacuo, and suspended with silica gel (50% wt). The silica plug was washed with dichloromethane, and the combined organics were concentrated in vacuo while co-evaporating with methanol to provide 4-(benzyloxy)-4-oxobutyl((benzyloxy)carbonyl)-L-valinate (2b) in 76.7% yield.

Step 3: Preparation of 4-((L-valyl)oxy)butanoic acid

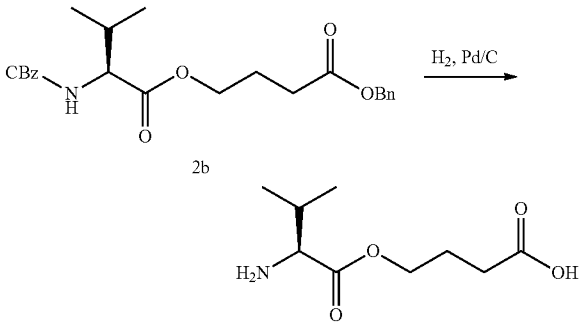

2b

1

4-(Benzyloxy)-4-oxobutyl((benzyloxy)carbonyl)-L-valinate (2b) (1.0 equivalent) was dissolved in methanol (5 volumes) and Pd/C (10% Pd, 15% wt) was added under a nitrogen atmosphere. The nitrogen atmosphere was replaced with a continuous flow of $H_2$ and the reaction mixture was stirred for 16 hours at room temperature. The reaction mixture was filtered over Celite® (50% wt) and stirred for 18 hours with activated carbon (25% wt). The reaction mixture was filtered over Celite® (50% wt) and the filter cake was rinsed with methanol. The reaction mixture was concentrated in vacuo while co-evaporating with methanol. The residue was redissolved in tert-butyl methyl ether and stirred for 30 minutes at room temperature. Another portion of tert-butyl methyl ether (3 volumes) was added dropwise within 2 hours. The reaction mixture was stirred for 4 hours and filtered. The filter cake was dried in vacuo to provide 4-((L-valyl)oxy)butanoic acid in 49.6% yield.

Example 3

Crystallization of 4-((L-Valyl)oxy)butanoic Acid

About 25 mg of 4-((L-valyl)oxy)butanoic acid was weighed into an 8 mL glass vial, and an appropriate amount of water or methanol was added to dissolve the solid with stirring. After complete dissolution, a set amount of anti-solvent was slowly added over a duration of about 30 minutes.

The solvent was either water or methanol, and suitable antisolvents include acetonitrile, isopropanol, acetone ethyl acetate, methyl tert-butyl ether, and 1,4-dioxane.

About 50 mg or 100 mg of 4-((L-valyl)oxy)butanoic acid was weighed into a glass vial, an appropriate amount (80 μL to 300 μL) of solvent was added, and the vial was warmed to a set temperature while stirring. After the set temperature was reached, the same solvent was slowly added to the suspension until the sample dissolved completely, or an appropriate amount of anti-solvent was slowly added to the clear solution. The solution was stirred at the set temperature for about 30 minutes, and the solution was then slowly cooled to room temperature (20° C. to 25° C.). The solid precipitate was collected by filtration. The solvent was ethanol, 50:1 ethanol/water, water, methanol, or isopropanol. The antisolvent, if used, was acetone ethyl acetate or methyl tert-butyl ether. The solvent can be methanol and the anti-solvent can be methyl tert-butyl ether. The volume ratio of methanol to methyl tert-butyl ether can be bout 1:3.

Example 4

X-Ray Powder Diffraction (XPRD) of Crystalline 4-((L-Valyl)oxy)butanoic Acid The X-ray powder diffraction (XRPD) pattern of crystalline 4-((L-valyl)oxy)butanoic acid was obtained using a Bruker D8 Advance X-ray powder diffractometer. The 20 position was calibrated against a Panalytical Si standard disc. The X-ray wavelength was Kα2/Kα1 (1.540598Å/1.544425 Å) at a 0.5 intensity ratio. The X-ray tube was set at an output voltage of 40 kV and a current of 40 mA. A ⅛° fixed divergence slit was used, and the diffraction patterns were obtained from 3° to 40° (°2θ) in a continuous scan mode using a step size of 0.02° (2θ) and a scan speed of 0.145 deg/min. The samples were transferred from a sample container onto a zero background XRPD-holder and gently ground to provide a smooth surface.

A representative XPRD diffraction pattern of crystalline 4-((L-valyl)oxy)butanoic acid is shown in FIG. 1 and the characteristic diffraction peaks are listed in Table 1.

TABLE 1

Characteristic peaks of the XRPD pattern.

| Peak Index | Angle (°2θ) | Relative Intensity (%) |
|---|---|---|
| 1 | 6.79 | 1.5 |
| 2 | 8.28 | 100.0 |
| 3 | 9.58 | 14.6 |
| 4 | 11.63 | 7.2 |
| 5 | 12.65 | 0.6 |
| 6 | 13.75 | 12.9 |
| 7 | 14.15 | 2.0 |
| 8 | 15.75 | 1.4 |
| 9 | 16.75 | 83.6 |
| 10 | 17.64 | 22.1 |
| 11 | 17.93 | 8.0 |
| 12 | 18.31 | 40.1 |
| 13 | 19.42 | 27.4 |
| 14 | 20.12 | 2.2 |
| 15 | 20.79 | 19.2 |
| 16 | 21.19 | 4.2 |
| 17 | 22.22 | 8.7 |
| 18 | 22.94 | 1.5 |
| 19 | 23.58 | 9.4 |
| 20 | 23.85 | 2.3 |
| 21 | 24.98 | 16.5 |
| 22 | 25.33 | 45.7 |
| 23 | 26.08 | 29.5 |
| 24 | 27.43 | 2.3 |
| 25 | 27.88 | 5.3 |
| 26 | 28.39 | 0.6 |
| 27 | 28.77 | 1.7 |
| 28 | 29.40 | 2.1 |
| 29 | 30.11 | 5.3 |
| 30 | 30.87 | 2.2 |
| 31 | 32.05 | 1.4 |
| 32 | 32.81 | 0.9 |
| 33 | 33.41 | 1.9 |
| 34 | 33.82 | 2.9 |
| 35 | 34.81 | 1.4 |
| 36 | 35.36 | 1.9 |
| 37 | 36.49 | 0.6 |
| 38 | 37.57 | 3.0 |
| 39 | 38.24 | 3.6 |
| 40 | 38.89 | 1.1 |

Example 5

Differential Scanning Calorimetry

Differential scanning calorimetry was performed using a TA Instruments Q2000 DSC and calibrated with an indium reference standard. Samples were loaded into crimped aluminum pans. Following equilibration at 25° C., the samples were heated under a nitrogen ($N_2$) atmosphere at a rate of 50 mL/min to a final temperature of 250° C. The scan rate was 10° C./min. DSC curves are shown in FIG. 2 and reflect an onset melting temperature of 137.73° C. and a peak melting temperature for crystalline 4-((L-valyl)oxy)butanoic acid of 139.88° C.

Example 6

Thermogravimetric Analysis

Thermogravimetric analysis was performed using a TA Instruments Q500 TGA calibrated using a nickel reference standard. Samples were placed in an open platinum or aluminum pan and after equilibrating at 35° C., the samples were heated under a nitrogen ($N_2$) atmosphere (60 mL/min flow rate) at a rate of 10° C./min to a final temperature of 200° C. TGA curves for crystalline is shown in FIG. 3 show a weight loss of 9.7% between 125° C. to 150° C. The weight loss form 30° C. to 125° C. was 0.77%.

The TGA thermogram shows that the crystalline 4-((L-valyl)oxy)butanoic acid did not undergo any appreciable weight loss prior to melting, which indicated that the crystalline form was anhydrous.

Example 7

Jet Milling

Crystalline 4-((L-valyl)oxy)butanoic acid was jet milled to obtain a uniform particle size distribution centered at a about 8.6 μm. An Alpine 50AS (PDS-PL-JM-01) Jet Mill (Hosokawa Alpine) was used to prepare the formulation. The injector gas pressure was 4.0 Bar and the grinding gas pressure was 3.5 Bar. Five (5) gm of crystalline 4-((L-valyl)oxy)butanoic acid was gradually added to the jet mill and the milled product collected. The milled product was stored at a temperature from 2° C. to 8° C.

Example 8

Sealed Storage Stability

Crystalline 4-((L-valyl)oxy)butanoic acid was packaged in double low-density polyethylene (LDPE) zipper bags and sealed. The packaged samples were then placed within an aluminum foil outer bag (polyethylene, polyethylene terephthalate three-layer composite) and sealed. The fully packaged samples were placed in stability chambers for the duration of the sealed storage stability study.

Sealed storage stability studies were carried out under four sets of conditions external to the packaged crystalline 4-((L-valyl)oxy)butanoic acid:

1. Accelerated conditions (4°±2° C., 75±5% RH).
2. Intermediate storage condition (3°±2° C., 65±5% RH).
3. Long-term storage condition (25±2° C., 6°±5% RH).
4. 2-8° C. conditions.

The sealed storage stability of crystalline 4-((L-valyl)oxy)butanoic acid (1) was tested according to the International Council for Harmonization of Technical Requirements for Pharmaceuticals for Human Use (ICH) document Q1A (R2) "Stability Testing of New Drug Substances and Products." Accordingly, samples were pulled at 3- and 6-month time-points. The assay percentage of the crystalline 4-((L-valyl)oxy)butanoic acid was determined by electrochemical titration using acetic acid as the solvent and perchloric acid as the titrant. Water content was tested by Karl Fischer titration (Karl Fisher Titrator: Mettler V30). Impurities were measured by HPLC (HPLC Instrument: Waters Arc HPLC system with CAD; Column: Waters Atlantis T3, 4.6×150 mm, 3 μm). The samples were analyzed by XRPD analysis (XRPD Instrument: Bruker D8 advance). The sealed storage stability results of crystalline 4-((L-valyl)oxy)butanoic acid stored under the four storage conditions are summarized in Table 2.

TABLE 2

Sealed storage stability of crystalline 4-((L-valyl)oxy)butanoic acid.

| | Storage Conditions | | | | | | | | | | | |
|---|---|---|---|---|---|---|---|---|---|---|---|---|
| | 2-8° C. | | | 25 ± 2° C., 60 ± 5% RH | | | 30 ± 2° C., 65 ± 5% RH | | | 40 ± 2° C., 75 ± 5% RH | | |
| | D 0 | 3 M | 6 M | D 0 | 3 M | 6 M | D 0 | 3 M | 6 M | D 0 | 3 M | 6 M |
| Assay (wt %) | 99.4 | 98.8 | 99.8 | 99.4 | 98.8 | 99.3 | 99.4 | 99.9 | 99.3 | 99.4 | 98.8 | 99.3 |
| Total Impurities (wt %) | 0.3 | 0.4 | 0.2 | 0.3 | 0.5 | 0.4 | 0.3 | 0.4 | 0.4 | 0.3 | 0.6 | 0.7 |
| Water Content (wt %) | 0.1 | 0.2 | 0.3 | 0.1 | 0.2 | 0.3 | 0.1 | 0.4 | 0.1 | 0.1 | 0.1 | 0.3 |
| Crystalline Form | C | N/A | C | C | N/A | C | C | C | C | C | N/A | C |

Note:
D = day, M = month, C = Conforms, N/A = Not Applicable.

The sealed storage stability study results indicated that crystalline 4-((L-valyl)oxy)butanoic acid was stable up to 6 months under all sealed storage conditions. The crystalline sample was also chemically stable up to 6 months under all sealed storage conditions.

In other studies, crystalline 4-((L-valyl)oxy)butanoic acid was demonstrated to be sealed storage stable at 25±2° C., 6°±5% RH for 36 months. Stability is defined as the sample of crystalline 4-((L-valyl)oxy)butanoic acid absorbs less than 2 wt % water and an impurity content of less than 2 wt % for a period of time under the indicated sealed storage conditions.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A crystalline form of 4-((L-valyl)oxy) butanoic acid:

(1)

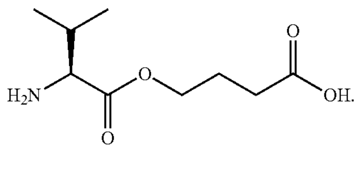

wherein the crystalline form is characterized by an XRPD pattern comprising characteristic diffraction peaks at least at 8.28°±0.20°, 16.75°±0.20°, and 25.33°±0.20° expressed as °2θ angles determined using Cu-Kα radiation.

2. The crystalline form of claim 1, wherein the crystalline form is characterized by an XRPD pattern comprising characteristic diffraction peaks at least at 8.28°±0.20°, 16.75°±0.20°, 17.64°±0.20°, 18.31°±0.20°, 19.42°±0.20°, 20.79°±0.20°, 25.33°±0.20°, and 26.08°±0.20° expressed as °2θ angles determined using Cu-Kα radiation.

3. The crystalline form of claim 1, wherein the crystalline form is characterized by an XRPD pattern comprising characteristic diffraction peaks at least at 8.28°±0.20°, 9.58°±0.20°, 13.75°±0.20°, 16.75°±0.20°, 17.64°±0.20°, 18.31°±0.20°, 19.42°±0.20°, 20.79°±0.20°, 24.98°±0.20°, 25.33°±0.20°, and 26.08°±0.20° expressed as °2θ angles determined using Cu-Kα radiation.

4. The crystalline form of claim 1, wherein the crystalline form has a weight loss from 0.16 wt % to 0.36 wt % over a temperature range from 20° C. to 70° C., wherein the weight loss is determined by thermogravimetric analysis at a scan rate of 2° C./min.

5. The crystalline form of claim 1, wherein the un-milled crystalline form has a bulk density from 0.15 g/mL to 0.25 g/mL, wherein bulk density is determined according to USP 616, Method 1.

6. The crystalline form of claim 1, wherein the un-milled crystalline form has a Hausner ratio from 1.65 to 1.95, wherein the Hausner ratio is determined according to USP 1174.

7. A granulation comprising a plurality of granules comprising the crystalline form of claim 1.

8. The granulation of claim 7, wherein the granules comprise greater than 80 wt % of the crystalline form, wherein wt % is based on the total weight of the granules.

9. The granulation of claim 7, wherein the granules comprise a core comprising greater than 80 wt % of the crystalline form, and a modified release coating surrounding the core, wherein wt % is based on the total weight of the core.

10. A pharmaceutical composition comprising the crystalline form of claim 1.

11. The pharmaceutical composition of claim 10, wherein the pharmaceutical composition comprises a therapeutically effective amount of the crystalline form for treating a disease in a patient, wherein the disease is selected from narcolepsy, cataplexy, cataplexy with narcolepsy, excessive daytime sleepiness, a sleep disorder associated with Parkinson's disease, Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep initiation and maintenance disorders, and chronic fatigue syndrome.

12. The pharmaceutical composition of claim 10, wherein the pharmaceutical composition comprises an oral formulation.

13. The pharmaceutical composition of claim 10, wherein the pharmaceutical composition comprises an immediate release component and a modified release component.

14. The pharmaceutical composition of claim 13, wherein the immediate release component comprises a solution comprising 4-((L-valyl)oxy) butanoic acid.

15. The pharmaceutical composition of claim 13, wherein the immediate release component comprises immediate release granules comprising the crystalline form of claim 1.

16. The pharmaceutical composition of claim 13, wherein the modified release component comprises modified release granules comprising the crystalline form of claim 1.

17. A method of treating a disease in a patient comprising administering to a patient in need of such treatment a therapeutically effective amount of the crystalline form of claim 1, wherein the disease is selected from narcolepsy, cataplexy, cataplexy with narcolepsy, excessive daytime sleepiness, a sleep disorder associated with Parkinson's disease, Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep initiation and maintenance disorders, and chronic fatigue syndrome.

18. A method of treating a disease in a patient comprising administering to a patient in need of such treatment a therapeutically effective amount of the crystalline form of claim 1, wherein the disease is selected from excessive daytime sleepiness associated with narcolepsy, excessive daytime sleepiness associated with Parkinson's disease, excessive daytime sleepiness associated with multiple sclerosis, fatigue associated with Parkinson's disease, fatigue associated with multiple sclerosis, fibromyalgia, insomnia associated with schizophrenia, and idiopathic hypersomnia.

19. A crystalline form of 4-((L-valyl)oxy) butanoic acid:

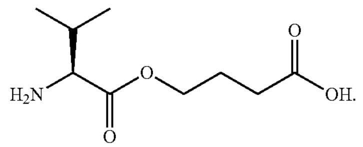

(1)

wherein the crystalline form has a melting enthalpy from 197 J/g to 207 J/g, wherein the melting enthalpy is determined by differential scanning calorimetry.

20. A granulation comprising a plurality of granules comprising the crystalline form of claim 19.

21. A pharmaceutical composition comprising the crystalline form of claim 19.

22. The pharmaceutical composition of claim 21, wherein the pharmaceutical composition comprises a plurality of granules comprising the crystalline form of claim 2.

23. A method of treating a disease in a patient comprising administering to a patient in need of such treatment a therapeutically effective amount of the crystalline form of claim 19, wherein the disease is selected from narcolepsy, cataplexy, cataplexy with narcolepsy, excessive daytime sleepiness, a sleep disorder associated with Parkinson's disease, Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep initiation and maintenance disorders, and chronic fatigue syndrome.

24. A method of treating a disease in a patient comprising administering to a patient in need of such treatment a therapeutically effective amount of the crystalline form of claim 19, wherein the disease is slected from excessive daytime sleepiness associated with narcolepsy, excessive daytime sleepiness associated with Parkinson's disease, excessive daytime sleepiness associated with multiple sclerosis, fatigue associated with Parkinson's disease, fatigue associated with multiple sclerosis, fibromyalgia, insomnia associated with schizophrenia, and idiopathic hypersomnia.

25. A crystalline form of 4-((L-valyl)oxy) butanoic acid:

(1)

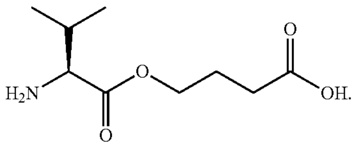

wherein the crystalline form has a melting peak temperature from 138.0° C. to 142.0° C., wherein the melting peak temperature is determined by differential scanning calorimetry.

26. A granulation comprising a plurality of granules comprising the crystalline form of claim 25.

27. A pharmaceutical composition comprising the crystalline form of claim 25.

28. The pharmaceutical composition of claim 27, wherein the pharmaceutical composition comprises a plurality of granules comprising the crystalline form of claim 25.

29. A method of treating a disease in a patient comprising administering to a patient in need of such treatment a therapeutically effective amount of the crystalline form of claim 25, wherein the disease is selected from narcolepsy, cataplexy, cataplexy with narcolepsy, excessive daytime sleepiness, a sleep disorder associated with Parkinson's disease, Parkinson's disease, a neurodegenerative disease, sleep disturbance syndrome, fatigue, improving nocturnal sleep, hypnagogic hallucinations, sleep paralysis, fragmented sleep, alcohol withdrawal and dependence, obstructive sleep apnea syndrome, insomnia, insomnia associated with schizophrenia, sleep initiation and maintenance disorders, and chronic fatigue syndrome.

30. A method of treating a disease in a patient comprising administering to a patient in need of such treatment a therapeutically effective amount of the crystalline form of claim 25, wherein the disease is selected from excessive daytime sleepiness associated with narcolepsy, excessive daytime sleepiness associated with Parkinson's disease, excessive daytime sleepiness associated with multiple sclerosis, fatigue associated with Parkinson's disease, fatigue associated with multiple sclerosis, fibromyalgia, insomnia associated with schizophrenia, and idiopathic hypersomnia.

* * * * *